US005578026A

United States Patent [19]
Lavash et al.

[11] Patent Number: 5,578,026
[45] Date of Patent: Nov. 26, 1996

[54] ABSORBENT ARTICLE HAVING A UNITARY RELEASE MATERIAL

[75] Inventors: Bruce W. Lavash, West Chester; Thomas W. Osborn, III, Cincinnati, both of Ohio; Kaoru Niihara, Ashiya, Japan

[73] Assignee: The Procter & Gamble Company, Cincinnati, Ohio

[21] Appl. No.: 402,769

[22] Filed: Mar. 13, 1995

Related U.S. Application Data

[63] Continuation of Ser. No. 283,925, Aug. 1, 1994, abandoned, which is a continuation of Ser. No. 906,593, Jun. 30, 1992, abandoned, which is a division of Ser. No. 915,202, Jul. 13, 1992, Pat. No. 5,366,504, which is a continuation-in-part of Ser. No. 886,518, May 20, 1992, Pat. No. 5,405,378.

[51] Int. Cl.$^6$ .............................. A61F 13/15; A61F 13/20
[52] U.S. Cl. ...................... 604/390; 604/385.1; 604/386; 604/387; 604/389
[58] Field of Search ................................ 604/358, 385.1, 604/385.2, 386, 387, 389–390

[56] References Cited

U.S. PATENT DOCUMENTS

| | | |
|---|---|---|
| D. 327,319 | 6/1992 | Ruffo et al. . |
| 3,245,855 | 4/1966 | Stenvall . |
| 3,397,697 | 8/1968 | Rickard . |
| 3,800,796 | 4/1974 | Jacob .................... 604/385.2 |
| 3,862,634 | 1/1975 | Small ........................ 604/390 |
| 3,913,580 | 10/1975 | Ginocchio . |
| 3,926,191 | 12/1975 | Tritsch ...................... 604/390 |
| 3,929,134 | 12/1975 | Karami . |
| 3,937,221 | 2/1976 | Tritsch ...................... 604/390 |
| 3,943,609 | 3/1976 | Egan, Jr. . |
| 3,967,624 | 7/1976 | Milnamow . |
| 4,166,464 | 9/1979 | Korpman . |
| 4,285,343 | 8/1981 | McNair . |
| 4,299,223 | 11/1981 | Cronkrite . |
| 4,327,732 | 5/1982 | Thinnes . |
| 4,496,359 | 1/1985 | Pigneul . |
| 4,589,876 | 5/1986 | Van Tilburg . |
| 4,596,570 | 6/1986 | Jackson et al. . |
| 4,597,759 | 7/1986 | Johnson . |
| 4,605,404 | 8/1986 | Sneider . |
| 4,608,047 | 8/1986 | Mattingly . |
| 4,615,696 | 10/1986 | Jackson et al. . |
| 4,654,040 | 3/1987 | Luceri . |
| 4,687,478 | 8/1987 | Van Tilburg . |
| 4,690,680 | 9/1987 | Higgins . |
| 4,701,171 | 10/1987 | Boland et al. . |
| 4,701,174 | 10/1987 | Johnson . |
| 4,701,178 | 10/1987 | Glaug . |
| 4,704,114 | 11/1987 | Wilson et al. . |
| 4,747,846 | 5/1988 | Boland et al. . |
| 4,756,709 | 7/1988 | Stevens . |
| 4,787,896 | 11/1988 | Houghton et al. . |
| 4,790,838 | 12/1988 | Pigneul et al. . |
| 4,795,455 | 3/1989 | Luceri et al. . |
| 4,834,739 | 5/1989 | Linker et al. . |
| 4,857,067 | 8/1989 | Wood et al. . |
| 4,900,319 | 2/1990 | Richwine . |

(List continued on next page.)

FOREIGN PATENT DOCUMENTS

| | | |
|---|---|---|
| 76104512 | 8/1987 | China . |
| 79205822 | 4/1989 | China . |
| 79202379 | 5/1989 | China . |
| 0464855A1 | 1/1992 | European Pat. Off. . |
| 0472376A1 | 2/1992 | European Pat. Off. . |
| 0471587 | 2/1992 | European Pat. Off. . |
| 0471587A1 | 2/1992 | European Pat. Off. . |
| 0471385A1 | 2/1992 | European Pat. Off. . |
| 0471384A1 | 2/1992 | European Pat. Off. . |

(List continued on next page.)

*Primary Examiner*—John G. Weiss
*Assistant Examiner*—P. Zuttarelli
*Attorney, Agent, or Firm*—Jeffrey V. Bamber; Steven W. Miller; Jacobus C. Rasser

[57] ABSTRACT

An absorbent article having a main body portion, a pair of flaps joined to the main body portion, and a unitary release material joined to a portion of each of the flaps such that the unitary release material superposes the flap adhesive when the flap is folded along a fold line.

17 Claims, 11 Drawing Sheets

U.S. PATENT DOCUMENTS

| | | |
|---|---|---|
| 4,900,320 | 2/1990 | McCoy . |
| 4,911,701 | 3/1990 | Mavinkurve . |
| 4,917,697 | 4/1990 | Osborn, III et al. . |
| 4,936,839 | 6/1990 | Molee et al. . |
| 4,940,462 | 7/1990 | Salerno . |
| 4,944,735 | 7/1990 | Mokry . |
| 4,985,025 | 1/1991 | Lingertat et al. . |
| 5,080,658 | 1/1992 | Igaue et al. . |
| 5,087,254 | 2/1992 | Davis et al. ............... 604/358 |
| 5,133,705 | 7/1992 | Nakanishi et al. . |
| 5,135,521 | 8/1992 | Luceri et al. . |
| 5,151,091 | 9/1992 | Glaug et al. . |
| 5,281,209 | 1/1994 | Osborn, III et al. . |
| 5,324,278 | 6/1994 | Vissdier et al. . |
| 5,344,416 | 9/1994 | Niihara . |
| 5,346,486 | 9/1994 | Osborn, III et al. . |
| 5,354,400 | 10/1994 | Lavash et al. . |
| 5,389,094 | 2/1995 | Lavash et al. . |
| 5,472,437 | 12/1995 | Akiyama et al. ............ 604/385.1 |

FOREIGN PATENT DOCUMENTS

| | | |
|---|---|---|
| 1491234 | 4/1969 | Germany . |
| 3319421 | 11/1984 | Germany . |
| 3326026 | 2/1985 | Germany ............... 604/389 |
| 63-143328 | 9/1988 | Japan . |
| 63-180031 | 11/1988 | Japan . |
| 3-46316 | 4/1991 | Japan . |
| 4-126145 | 4/1992 | Japan . |
| 4-83231 | 7/1992 | Japan . |
| 5-21936 | 3/1993 | Japan . |
| 5-24026 | 3/1993 | Japan . |
| 5-95975 | 4/1993 | Japan . |
| 5-103813 | 4/1993 | Japan . |
| 2118021 | 10/1983 | United Kingdom . |
| 2151460 | 7/1985 | United Kingdom . |
| WO89/02729 | 4/1989 | WIPO . |
| WO92/18080 | 10/1992 | WIPO . |
| WO92/17139 | 10/1992 | WIPO . |

ABSORBENT ARTICLE HAVING A UNITARY RELEASE MATERIAL

This is a continuation Ser. No. 08/283,925, filed on Aug. 1, 1994 now abandoned, which is a continuation of application Ser. No. 07/906,593 filed Jun. 30, 1992, now abandoned which is a divisional of application Ser. No. 07/915,202 filed Jul. 13, 1992, now U.S. Pat. No. 5,366,504, which is a continuation in part application of application Ser. No. 07/886,518 filed May 20, 1992, now U.S. Pat. No. 5,405,378.

FIELD OF THE INVENTION

The present invention relates to disposable absorbent articles, such as sanitary napkins, adult incontinence devices, and the like. Still more particularly, the present invention concerns such disposable absorbent articles having side flaps and flap adhesive for joining the flaps to the underside of a wearer's panty.

BACKGROUND OF THE INVENTION

All manner and variety of absorbent articles configured for the absorption of body fluids such as menses, urine, and feces are, of course, well known. Absorbent articles, particularly sanitary napkins, having wings or flaps are disclosed in the literature and are available in the marketplace.

Generally, the flaps extend laterally from a central absorbent means and are intended to be folded around the edges of the wearer's panties in the crotch region. Thus, the flaps are disposed between the edges of the wearer's panties in the crotch region and the wearer's thighs.

The flaps serve at least two purposes. First, the flaps prevent exudates which otherwise would soil the edges of the wearer's panties from doing such. Second, the flaps help stabilize the napkin from shifting out of place, especially when the flaps are affixed to the underside of the panties.

Sanitary napkins having flaps of various types are disclosed in U.S. Pat. No. 4,687,478, entitled "Shaped Sanitary Napkin With Flaps", which issued to Van Tilburg on Aug. 18, 1987, U.S. Pat. No. 4,608,047, entitled "Sanitary Napkin Attachment Means", which issued to Mattingly on Aug. 26, 1986, U.S. Pat. No. 4,589,876, entitled "Sanitary Napkin", which issued to Van Tilburg on May 20, 1986, U.S. Pat. No. 4,285,343, entitled "Sanitary Napkin", which issued to McNair on Aug. 25, 1981, U.S. Pat. No. 3,397,697, entitled "Disposable Sanitary Shield For Undergarments", which issued to Rickard on Aug. 20, 1968, and U.S. Pat. No. 2,787,271, entitled "Sanitary Napkin", which issued to Clark on Apr. 2, 1957.

Commonly, the flaps are provided with an adhesive attachment means, or flap adhesive, for affixing the flaps to the underside of the wearer's panties. The flap adhesive is generally provided with a release liner to protect the adhesive from dirt, keep the adhesive from drying out and to keep it from sticking to extraneous surfaces prior to use. The release liner is peeled from the flap adhesive to expose the adhesive surface which is then applied to the underside of the panties to secure the flap in place. After being peeled from the flap adhesive, the release liner is discarded. However, this arrangement requires the use of two hands to remove the release liner from each flap, i.e., the user must hold the flap with one hand and peel the release liner with the other hand. This also requires the user to dispose of the release liners which have been removed from the flaps of the sanitary napkin. Therefore, there is a need for a sanitary napkin having flaps which can be manipulated and applied using one hand. There is also a need for a sanitary napkin with a protective release material which does not have to be thrown-away or discarded.

While flaps greatly improve the effectiveness of a sanitary napkin, the flaps of a sanitary napkin may hinder or impede application of the sanitary napkin to the crotch of the wearer's panty. Currently, each of the flaps of a sanitary napkin have an end, the distal end, which may move freely relative to the sanitary napkin. Once the release paper of the central pad adhesive is removed by the wearer, the distal ends of the flaps may fall between the crotch portion of the wearer's panty and the sanitary napkin and may become adhered to the central pad adhesive. Therefore, there is a need for a sanitary napkin having flaps positioned so that they will not interfere with the application of the sanitary napkin to the panty.

Accordingly, it is an object of the present invention to provide an absorbent article, such as a sanitary napkin, having folded flaps and a unitary release material for the flap adhesive which allows the flap adhesive to be exposed using only one hand, eliminates the need to dispose of pieces of release liner, and maintains the flap in a folded configuration until the flap is used, so that the flap will not interfere with the application of the sanitary napkin to the panty.

It is also an object of the present invention to provide an absorbent article, such as a sanitary napkin, having flaps which are folded and tucked into a recessed area and having an unitary release material for the flap adhesive.

It is an additional object of the present invention to provide an absorbent article, such as a sanitary napkin, having folded flaps, an unitary release material, and zones of differential extensibility for relieving the stresses that develop in the flaps when they are folded down along the edges of the crotch of the wearer's undergarments and affixed to the underside of the undergarments.

It is an additional object of the present invention to provide an absorbent article having folded and tucked side flaps, an unitary release material, and zones of differential extensibility.

These and other objects of the present invention will be more readily apparent when considered in reference to the following description and when taken in conjunction with the accompanying drawings.

SUMMARY OF THE INVENTION

In accordance with the present invention, an absorbent article, such as a sanitary napkin, having folded flaps and an unitary release material, is provided. The absorbent article comprises a main body portion, a pair of flaps joined to the main body portion, and an unitary release material joined to a portion of the absorbent article such that the flap adhesive of at least one of the flaps is superposed by the unitary release material when the flap is folded along a fold line. The unitary release material may be joined to a portion of the flap or may be joined to any other portion of the absorbent article, such as the main body portion.

BRIEF DESCRIPTION OF THE DRAWINGS

FIG. 1a is a cross-sectional view of the sanitary napkin of FIG. 1 taken along section line 1a–1a.

FIG. 2a is a cross-sectional view of the sanitary napkin of FIG. 2 taken along section line 2a–1a.

FIG. 4 is a cross-sectional view of another sanitary napkin embodiment taken from an angle similar to that of FIG. 2a.

DETAILED DESCRIPTION OF PREFERRED EMBODIMENTS

1. Introduction

A. The Absorbent Article In General

Figure 1:
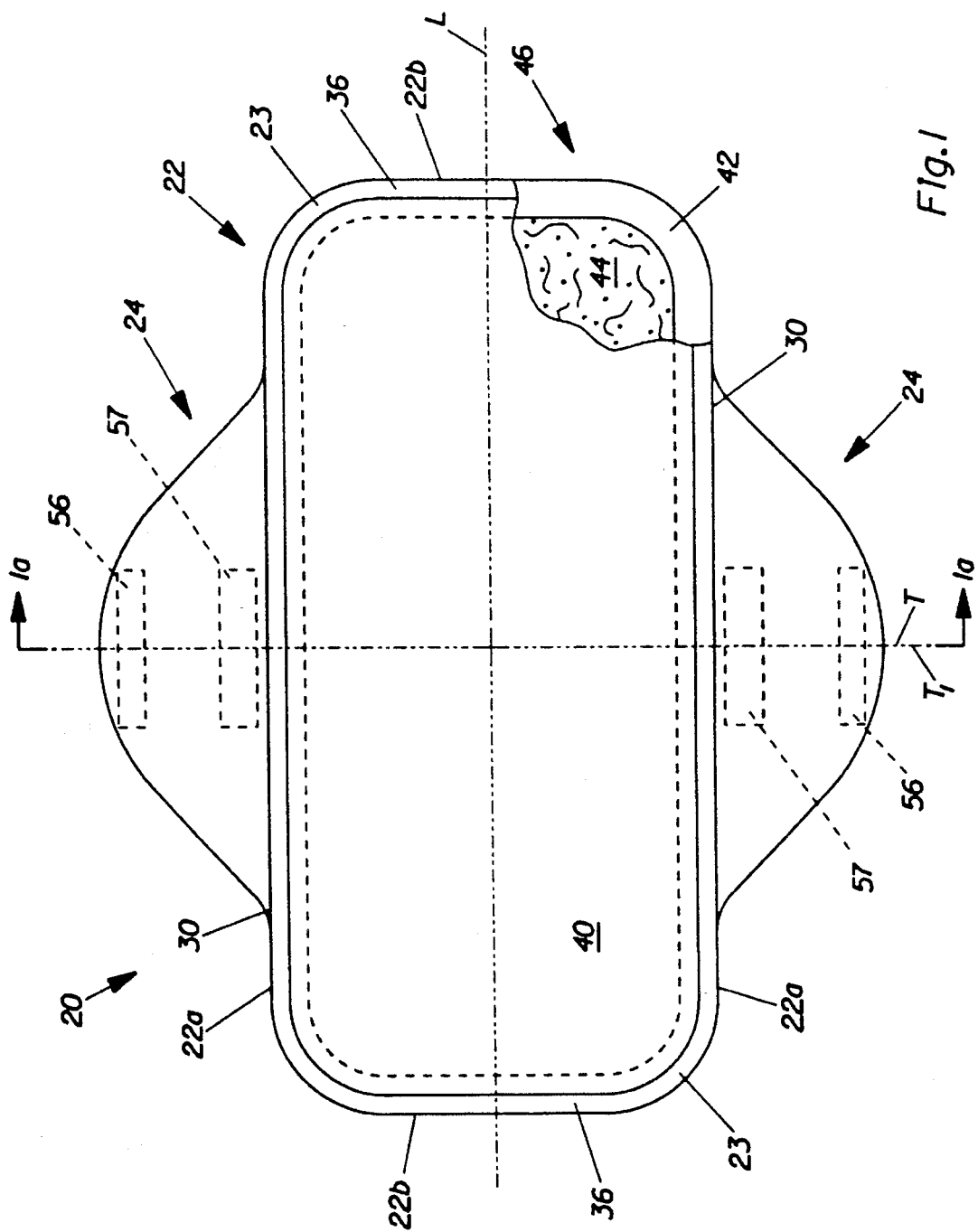
FIG. 1 is a top plan view of a sanitary napkin embodiment of the present invention having portions cut-away to show the absorbent core.

The present invention relates to disposable absorbent articles, such as female sanitary napkins. More particularly, the present invention relates to such disposable absorbent articles having flaps with a flap adhesive which secures the flap to the underside of a user's panty.

The term "absorbent article", as used herein, refers to articles which absorb and contain body exudates. More specifically, the term refers to articles which are placed against or in proximity to the body of the wearer to absorb and contain the various exudates discharged from the body. The term "absorbent article" is intended to include sanitary napkins, pantiliners, and incontinent pads (and other articles worn in the crotch region of a garment). The term "disposable" refers to articles which are intended to be discarded after a single use and preferably recycled, composted, or otherwise disposed of in an environmentally compatible manner. (That is, they are not intended to be laundered or otherwise restored or reused as an absorbent article.)

The term "sanitary napkin", as used herein, refers to an article which is worn by females adjacent to the pudendal region that is intended to absorb and contain the various exudates which are discharged from the body (e.g., blood, menses, and urine). The present invention, however, is not limited to the particular types or configurations of absorbent articles shown in the drawings.

As used herein, the terms "release material" or "release member" refer to any material which can be used to protect adhesives, such as the flap adhesives, from dirt, keep adhesives from drying out, and/or to keep adhesives from sticking to extraneous surfaces prior to use. As used herein, the terms "unitary release material" or "unitary release member" refer to a release material that is joined to a portion of the disposable absorbent article. As used herein, the term "joined" encompasses configurations whereby an element is directly secured to the other element by affixing the element directly to the other element; configurations whereby the element is indirectly secured to the other element by affixing the element to intermediate member(s) which in turn are affixed to the other element; and configurations whereby one element is integral with another element, i.e., one element is essentially part of the other element. Examples of joining a release member to the sanitary napkin would include: securing a release liner (such as the release liner 58 used for the central pad adhesive 54) to at least a portion of the sanitary napkin; applying (e.g., spraying, painting, impregnating, etc.) a substance, such as silicone, to at least a portion of the sanitary napkin; joining an element (i.e., backsheet, topsheet, flaps, etc.) to the sanitary napkin, which is comprised of a suitable material such that at least a portion of the element will function as a suitable release member; and the like. Part or all of the unitary release member 57 may be joined to the sanitary napkin 20. For example, the unitary release member 57 may be joined to the sanitary napkin by a perimeter bond, single or multiple bond lines, single or multiple spot bonds, or a surface bond wherein the entire surface of the unitary release 57 is bonded to a portion of the sanitary napkin 20.

A preferred embodiment of a sanitary napkin 20 of the present invention is shown in FIG. 1. As shown in FIG. 1, the sanitary napkin 20 basically comprises a main body portion 22 and two flaps 24 (shown in the extended position) joined to the main body portion 22. Each flap 24 comprises a flap adhesive 56 and a unitary release member 57. The main body portion 22 comprises an absorbent means represented by an absorbent assembly 46. In the preferred embodiment shown in FIG. 1, the unitary release member 57 will comprise a portion of the flap 24. However, the unitary release member 57 may comprise a portion of the main body portion 22, i.e., the topsheet 40, the backsheet 42, etc. (In the discussion that follows, unless otherwise noted, the sanitary napkin described herein will have two flaps. While it is not necessary that the napkin have two flaps, two flaps are preferred over one flap. Also, while it is not necessary that the flaps be mirror images of one another, they preferably are. Thus, the description of one flap will be a description of the other, and, for clarity, discussion of the second flap may be omitted.)

The sanitary napkin 20 has two centerlines, a principal longitudinal centerline L and a principal transverse centerline T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" used herein, are interchangeable, and refer to a line, axis or direction which lies within the plane of the sanitary napkin 20 that is generally perpendicular to the longitudinal direction.

Figure 1A:
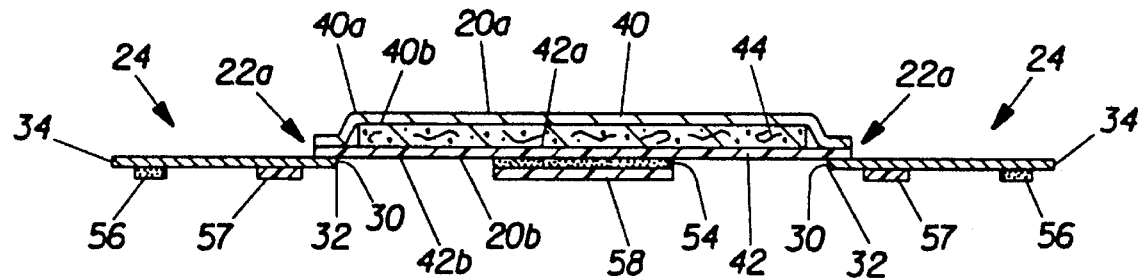

The sanitary napkin 20 is comprised of a topsheet 40, a backsheet 42, an absorbent core 44, and a pair of flaps 24. At least a part of the topsheet 40, backsheet 42, and absorbent core 44 comprise the absorbent assembly 46 of the main body portion 22. The flaps 24 shown in FIGS. 1 and 1a are comprised of discrete pieces of material which are affixed to the main body portion 22. (In alternative embodiments, such as those shown in U.S. Pat. No. 4,917,697 issued to Osborn, the flaps 24 may be integral with the main body portion 22. In such a case, the topsheet 40 may form one surface of both the flaps 24 and the main body portion 22, and the backsheet 42 may form the other surface of the same. In addition, the absorbent material of the sanitary napkin 20 may extend into the flaps 24 to form a flap absorbent core, as described in greater detail in U.S. Pat. No. 4,917,697.) In a particularly preferred embodiment, the main body portion 22 will additionally comprise a restraining member 78 which is joined to the absorbent assembly 46 to form a recessed area 68 between the restraining member 78 and the absorbent assembly 46 of the main body portion 22.

2. The Individual Components of the Absorbent Article

The individual components of the sanitary napkin 20 will first be looked at in greater detail.

A. The Topsheet

The topsheet 40 is liquid permeable and when the sanitary napkin 20 is in use, the topsheet 40 is in close proximity to the skin of the user. The topsheet 40 is compliant, soft feeling, and non-irritating to the user's skin. It can be made from any of the materials conventional for this type of use. Nonlimiting examples of suitable materials that can be used as the topsheet 40 are woven and nonwoven polyester, polypropylene, nylon, and rayon and formed thermoplastic films, with formed films being preferred.

Suitable formed films are described in U.S. Pat. No. 3,929,135, entitled "Absorptive Structure Having Tapered Capillaries", which issued to Thompson on Dec. 30, 1975, U.S. Pat. No. 4,324,426, entitled "Disposable Absorbent Article Having A Stain-Resistant Topsheet", which issued to Mullane and Smith on Apr. 13, 1982, U.S. Pat. No. 4,342,314, entitled "Resilient Plastic Web Exhibiting Fiber-Like Properties", which issued to Radel and Thompson on Aug. 3, 1982, and U.S. Pat. No. 4,463,045, entitled "Macroscopically Expanded Three-Dimensional Plastic Web Exhibiting Non-Glossy Visible Surface and Cloth-Like Tactile Impression", which issued to Ahr, Louis, Mullane, and Ouellette on Jul. 31, 1984. Formed films are preferred for the topsheet 40 because they are pervious to liquids and yet non-absorbent. Thus, the surface of the formed film which is in contact with the body remains dry and is more comfortable to the wearer.

The sanitary napkin 20 may also be comprised of components that are extensible (i.e., capable of stretching, particularly in the longitudinal direction) when the sanitary napkin is worn. The sanitary napkin 20 may capable of elongating between about 15% and about 40% of its unstretched length. This extensibility provides better in-use fit, comfort, and decreased staining. In other embodiments, only limited portions of the components of the sanitary napkin 20 are capable of stretching. Such an embodiment (without the unitary release material of the present invention) is described in greater detail in co-pending, commonly-assigned U.S. patent application Ser. No. 07/769,891, "Absorbent Article Having Flaps and Zones of Differential Extensibility", filed Oct. 1, 1991, in the name of Bruce Lavash, et al.

A particularly preferred topsheet 40 for use in such an embodiment is one which is made in accordance with U.S. Pat. No. 4,463,045 and ring rolled to provide it with a degree of longitudinal extensibility. Suitable processes for ring rolling or "pre-corrugating" are described in U.S. Pat. No. 4,107,364 issued to Sisson on Aug. 15, 1978, U.S. Pat. No. 4,834,741 issued to Sabee on May 30, 1989 and in co-pending, commonly assigned U.S. patent application Ser. No. 07/662,536 entitled "Improved Method And Apparatus For Incrementally Stretching A Zero Strain Stretch Laminate Web To Impart Elasticity Thereto" filed by Gerald M. Weber et al. on Feb. 28, 1991, U.S. patent Application Ser. No. 07/662,537 entitled "Improved Method and Apparatus For Incrementally Stretching Zero Strain Stretch Laminate Web In A Non-Uniform Manner To Impart A Varying Degree of Elasticity Thereto" filed by Kenneth B. Buell et al. on Feb. 28, 1991, and U.S. patent Application Ser. No. 07/662,543 entitled "Improved Method And Apparatus For Sequentially Stretching Zero Strain Stretch Laminate Web To Impart Elasticity Thereto Without Rupturing The Web" filed by Gerald M. Weber et al. on Feb. 28, 1991. The fold lines in the corrugations of the topsheet should run in the transverse direction so the topsheet is longitudinally extensible.

Such a topsheet is described in greater detail in the following patent applications which were filed on Jun. 23, 1991: U.S. patent application Ser. No. 07/734,404 entitled "Absorbent Articles, Especially Catamenials, Having Improved Fluid Directionality, Comfort and Fit" filed in the names of Thompson, et al.; U.S. patent application Ser. No. 07/734,392 entitled "Fluid Handling Structure for Use in Absorbent Articles" filed in the names of Thompson, et al.; and, U.S. patent application Ser. No. 07/734,405 entitled "Absorbent Core for Use in Catamenial Products" filed in the names of Buenger, et al. These patent applications may be referred to collectively as the "Capillary Channel Fiber" patent applications.

In addition, in preferred embodiments of the present invention, at least a portion of the outer surface 40a of the topsheet 40 is treated with a surfactant. It is preferred that the surfactant be substantially evenly and completely distributed across at least the portion of the outer surface 40a of topsheet 40 that overlays the main body portion 22. This can be accomplished by any of the common techniques well known to those skilled in the art. For example, the surfactant can be applied to topsheet 40 by spraying, by padding, or by the use of transfer rolls.

Treating the outer surface 40a of the topsheet 40 with a surfactant renders the surface of the topsheet 40 more hydrophilic. This results in liquid penetrating the topsheet 40 faster than it would if the surface were not treated. This diminishes the likelihood that menstrual fluids will flow off topsheet 40 rather than being absorbed by the absorbent core 44. Preferably, any portions of the topsheet 40 that overlay the flaps 24 are not treated with the surfactant. This will minimize any tendencies fluids may have to spread laterally across the flaps and to come in contact with the wearer's thighs and other parts of the wearer's body.

In preferred embodiments, the inner surface 40b of the topsheet 40 is secured in contacting relation with the absorbent core 44. This contacting relationship results in liquid penetrating the topsheet 40 faster than if the topsheet 40 were not in contact with the absorbent core 44. The topsheet 40 can be maintained in contact with the absorbent core 44 by applying adhesive to the inner surface 40b of the topsheet 40. Suitable adhesives useful for this purpose are described in U.S. Pat. No. 4,917,697. The adhesives can be applied by the same methods as the surfactant is applied to the outer surface 40a of the topsheet 40.

B. The Absorbent Core

The absorbent core 44 is positioned between the topsheet 40 and the backsheet 42. The absorbent core 44 provides the means for absorbing menstrual fluid. The absorbent core 44 need not have an absorbent capacity much greater than the total amount of menstrual fluid anticipated to be absorbed. The absorbent core 44 is generally compressible, conformable, and non-irritating to the user's skin. It can comprise any material used in the art for such purpose. Examples include comminuted wood pulp which is generally referred to as airfelt, creped cellulose wadding, absorbent foams, absorbent sponges, synthetic staple fibers, polymeric fibers, hydrogel-forming polymer gelling agents, peat moss, or any equivalent material or combinations of materials.

Polymeric gelling agents are those materials which, upon contact with fluids (i.e., liquids) such as water or body fluids, imbibe such fluids and thereby form hydrogels. In this manner, fluids discharged into the absorbent core 44 can be acquired and held by the polymeric gelling agent, thereby providing the articles herein with enhanced absorbent capacity and/or improved fluid retention performance.

The polymeric gelling agent which is employed in the absorbent core 44 will generally comprise particles of a substantially water-insoluble, slightly cross-linked, partially neutralized, hydrogel-forming polymer material. The term "particles", as used herein, can refer to particles in any form, such as in the form of pellets, flakes, or fibers. The characteristics of the absorbent core 44 (including, but not limited to the preferred types of polymer materials used therein, and types of methods which can be used for preparing these polymer particles) are described in greater detail in U.S. Pat. No. 5,009,653 issued to Osborn and the patents incorporated by reference in that patent, the disclosures of which are all incorporated by reference herein.

In one preferred embodiment, the absorbent core 44 is a laminate comprised of a layer of superabsorbent polymer material, such as in the form of particles, disposed between two air-laid tissues, first and second tissue layers (or "upper" and "lower" tissue layers). The first and second tissue layers provide containment of the superabsorbent polymer material, improve lateral wicking of the absorbed exudates throughout the absorbent core 44 and provide a degree of absorbency.

A suitable laminate is the superabsorbent laminate WATER-LOCK L-535 available from the Grain Processing Corporation of Muscatine, Iowa (WATER-LOCK registered TM by Grain Processing Corporation). Such superabsorbent laminates are disclosed in U.S. Pat. No. 4,467,012, entitled "Composition For Absorbent Film And Method Of Preparation", which issued to Pedersen et al. on Aug. 21, 1984, and U.S. Pat. No. 4,260,443, entitled "Laminated Absorbent Process", which issued to Lindsay et al. on Apr. 7, 1981.

The absorbent core 44 may be a laminate, as described above, which is slitted or partially slitted for longitudinal extensibility. This slitted or partially slitted core is described in greater detail in the Capillary Channel Fiber patent applications.

C. The Backsheet

The backsheet 42 is impervious to liquids and, thus, prevents menstrual fluid from soiling the clothing of the user. Any material used in the art for such purpose can be utilized herein. Suitable materials include embossed or non-embossed polyethylene films and laminated tissue. A suitable polyethylene film is manufactured by Monsanto Chemical Corporation and marketed in the trade as Film No. 8020.

In one alternative embodiment of the sanitary napkin 20 (typically in which the topsheet 40 overlays only the main body portion 22 and does not extend out to form the top surface of the flaps), the backsheet 42 may be comprised of two layers. In such a case, the backsheet 42 may comprise a first layer of lofted material disposed on the core-facing side 42a of the backsheet. The purpose of the first layer is to provide a comfortable, non-irritating surface against the body of the wearer. The lofted layer may be comprised of any suitable material, such as a nonwoven material. Preferably, the lofted layer comprises a hydrophobic nonwoven material. The second layer may be disposed on the garment side 42b of the backsheet 42, and may comprise a fluid impervious film. A low density polyethylene material about 0.01 to about 0.05 millimeters in thickness, preferably about 0.02 millimeters in thickness, has been found to work well as this second layer. A polyethylene film, such as is sold by the Ethyl Corporation, Visqueen Division, under model XP-39385 has been found particularly well suited for this second layer. The backsheet 42 may also be made of a soft, cloth-like material which is hydrophobic relative to the topsheet 40. A polyester or polyolefinic fiber backsheet 42 has been found to work well. A particularly preferred soft, cloth-like backsheet 42 material is a laminate of a polyester nonwoven material and a film such as described in U.S. Pat. No. 4,476,180 issued to Wnuk on Oct. 9, 1984.

A particularly preferred extensible backsheet 42 is an extended adhesive film Formula #198-338 manufactured by the Findley Adhesives Company of Wauwatosa, Wis. which is described in greater detail in the Capillary Channel Fiber patent applications.

3. Assembly of Components into a Sanitary Napkin and Formation of the Flaps

A. Assembly of Components

As shown in FIGS. 1 and 1a, the topsheet 40 is secured to the backsheet 42 along a first seam, such as seam 36. The seam 36 can be formed by any means commonly used in the art for this purpose such as by gluing, crimping, or heat-sealing. The seam 36 is illustrated in FIG. 1 as extending completely around the periphery 23 of the main body portion 22. This is a preferred embodiment for ease of construction. (Other means of uniting the various elements can be used.)

The main body portion 22 is the portion of the sanitary napkin 20 that contains an absorbent means, such as an absorbent core 44. The main body portion 22 has a liquid pervious body contacting surface (represented in FIG. 1a by the topsheet 40) and an opposed liquid impervious surface (represented in FIG. 1a by the backsheet 42). It is to be understood that the embodiment illustrated is only one possible embodiment, albeit a preferred one. Other possible embodiments include one in which an absorbent core 44 is essentially completely wrapped with topsheet before it is placed on a backsheet. The main body portion 22 can also comprise an absorbent core which possesses sufficient integrity to stand alone and is liquid pervious on one surface while the other surface has been treated to render it liquid impervious.

The main body portion 22 may be relatively thick or relatively narrow and thin. A narrow main body portion 22 may be effective because the overall configuration and use of the sanitary napkin 20 results in the main body portion 22 being maintained in close proximity to the body. Such proximity of the main body portion 22 places it precisely where it should be: very near the body at the vaginal opening. The main body portion 22 can then absorb the vast majority of the menstrual fluid (menses) before it has an opportunity to flow along the sides of the main body portion 22. A thin main body portion may also be desired because it is typically comfortable to the user.

FIGS. 1 and 1*a* also show the fasteners, such as adhesive attachment means, central pad adhesive 54 and flap adhesive 56, which are adapted to secure the sanitary napkin 20 to the crotch region of an undergarment.

The central pad adhesive 54 provides an adhesive attachment means for securing the main body portion 22 in the crotch portion of a panty. The outer surface of the flap 24, adjacent the distal edge 34 of the flap, is preferably coated with a flap adhesive 56. The flap adhesive 56 is used to assist in maintaining the flap 24 in position after it is wrapped around the edge of the crotch portion of the panty as described below. The flaps 24 can be maintained in position by attaching the flaps 24 to the undergarment, or to the opposing flap. Suitable adhesive fasteners are described in greater detail in U.S. Pat. No. 4,917,697.

The central pad adhesive 54 of the present invention is not limited to adhesive attachment means. Any type of fastener used in the art can be used for such purpose. For example, the main body portion 22 of sanitary napkin 20, could be secured to the wearer's undergarment by the fastener described in U.S. Pat. No. 4,946,527 entitled "Pressure-Sensitive Adhesive Fastener and Method of Making the Same" issued to Battrell on Aug. 7, 1990. The main body portion 22 of sanitary napkin 20, could also be secured to the wearer's undergarment by the fastener described in U.S. patent application Ser. No. 07/718,727, "Screen Printing Method For Manufacturing A Refastenable Mechanical Fastening System And Fastening System Produced Therefrom", filed Jun. 21, 1991, in the name of Dennis A. Thomas, et al., which patent applications are incorporated herein by reference. For simplicity, however, the fasteners will be described in terms of adhesive attachment means.

The central pad adhesive 54 is covered by a removable release liner, central pad release liner 58. The pressure-sensitive adhesive should be covered with a release liner to protect the adhesive from dirt, to keep the adhesive from drying out, and to keep the adhesive form sticking to extraneous surfaces prior to use. Suitable release liners are described in U.S. Pat. No. 4,917,697.

Figure 1B:
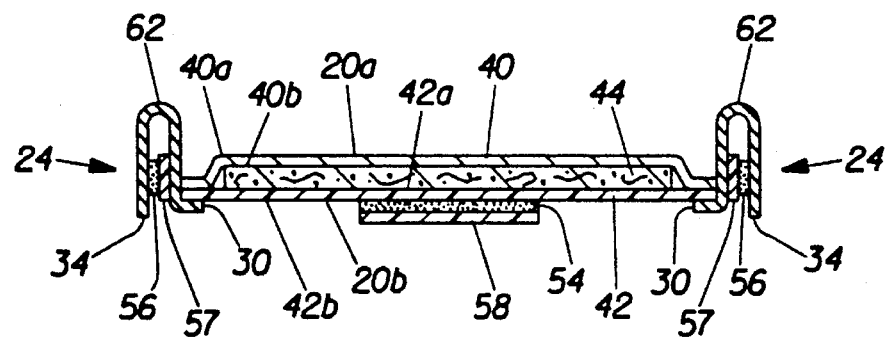
FIG. 1b is a cross-sectional view of the sanitary napkin of FIG. 1a showing the flaps in a folded configuration with the unitary release material superposing the flap adhesives.

The flap adhesive 56 is protected by the unitary release member 57, as shown in FIG. 1*b*. The unitary release member 57 is discussed in greater detail herein below.

While a preferred sanitary napkin embodiment of the present invention has been described, numerous other sanitary napkin embodiments having flaps are available and are disclosed in the literature. These could be provided with the unitary release material of the present invention. In particular, sanitary napkins having flaps are disclosed in U.S. patent application Ser. No. 07/707,233 entitled "Sanitary Napkin Having Laterally Extensible Means for Attachment to the Undergarment of the Wearer", filed May 21, 1991 in the name of Osborn, et al.; U.S. Pat. Nos. 5,009,653 and 4,950,264, both entitled "Thin, Flexible Sanitary Napkin" which issued to Osborn on Apr. 23, 1991 and Aug. 21, 1990, respectively, U.S. Pat. No. 4,917,697 entitled "Sanitary Napkin Having Flaps and Stress Relief Means" which issued to Osborn, III, et al. on Apr. 17, 1990, U.S. Pat. No. 4,687,478, entitled "Shaped Sanitary Napkin With Flaps", which issued to Van Tilburg on Aug. 18, 1987, U.S. Pat. No. 4,589,876, entitled "Sanitary Napkin", which issued to Van Tilburg on May 20, 1986, U.S. Pat. No. 4,285,343, entitled "Sanitary Napkin", which issued to McNair on Aug. 25, 1981, U.S. Pat. No. 3,397,697, entitled "Disposable Sanitary Shield For Undergarments", which issued to Rickard on Aug. 20, 1968, and U.S. Pat. No. 2,787,241, entitled "Sanitary Napkin", which issued to Clark on Apr. 2, 1957. All of the cited patents and patent applications are incorporated herein by reference.

Suitable absorbent articles in the form of pantiliners are disclosed in U.S. Pat. No. 4,738,676 entitled "Pantiliner" issued to Osborn on Apr. 19, 1988. Suitable absorbent articles, at least some of which are in the form of adult incontinence products, are described in U.S. patent application Ser. No. 07/637,571 entitled "Absorbent Article Having Rapid Acquiring Wrapped Multiple Layer Absorbent Body" filed by Barry R. Feist, et al. on Jan. 3, 1991.

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

B. Construction of the Flaps

The characteristics of the flaps 24 will now be looked at in greater detail. The general construction of flaps 24 suitable for use in the present invention (without the unitary release member 57 of the present invention) is described in greater detail in the patents incorporated by reference herein, such as U.S. Pat. No. 4,917,697 issued to Osborn; U.S. patent application Ser. No. 07/769,891, "Absorbent Article Having Flaps and Zones of Differential Extensibility", filed Oct. 1, 1991 in the name of Bruce Lavash, et al.; and U.S. patent application Ser. No. 07/832,246, "Absorbent Article Having Inwardly-Folded Pleated Flaps", filed Feb. 7, 1992 in the name of Kaoru Niihara and Thomas W. Osborn, III.

The overall size of the flaps 24 can be readily selected by those skilled in the art. Preferably, the flaps 24 are sized so that the sanitary napkin 20 is from about 10 to about 23 centimeters wide between the distal edges 34 of the flaps at their greatest separation. Preferably each flap 24 is from about 5 to at least about 19 centimeters long in the direction parallel to the principal longitudinal centerline L of the sanitary napkin. However, the flaps 24 may be as small as 0.5 centimeters long in the direction parallel to the principal longitudinal centerline L.

The shape of the flaps 24 can be selected by those skilled in the art. Preferably, not only are the flaps 24 mirror images of each other, the two halves of each flap 26 and 28 (shown in FIG. 3) are also symmetrical about the flap transverse centerline $T_1$. (It should be understood that the shape and orientation of the flaps described herein are those of a preferred embodiment. They are not mandatory design features.)

Figure 3:
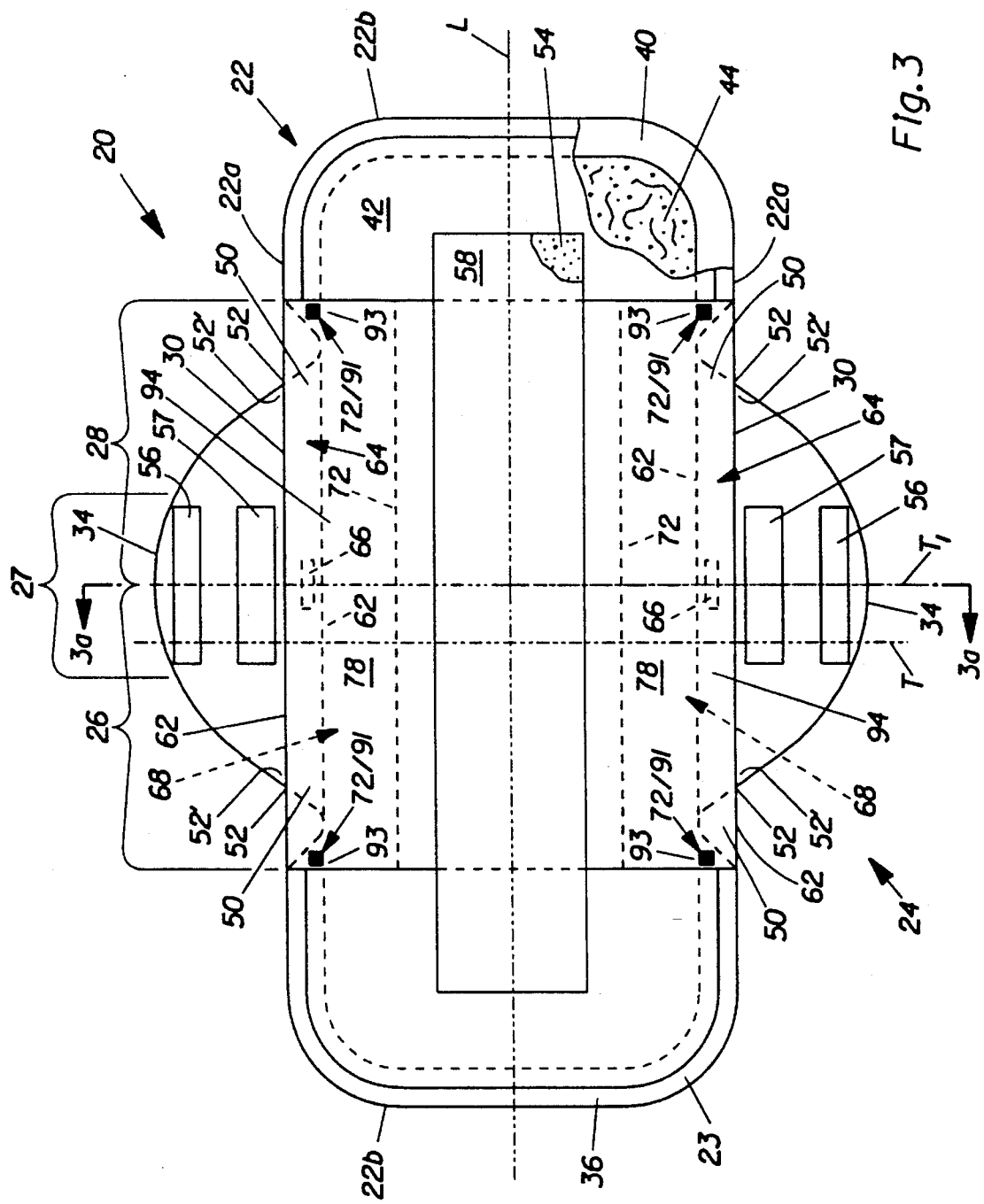
FIG. 3 is a plan view of an alternate sanitary napkin embodiment of the present invention.

Preferably, as in the sanitary napkin 20 illustrated in FIG. 3, the flaps 24 are positioned slightly forward of the principal transverse centerline T of the sanitary napkin. (In such a case, the flap transverse centerline $T_1$ does not coincide with the principal transverse centerline T of the sanitary napkin 20.) The flaps 24, however, are preferably evenly spaced from the principal longitudinal centerline L of the sanitary napkin.

In a preferred embodiment, the flaps 24 are joined with the main body portion 22 along lines of juncture 30. The lines of juncture can be concave, straight, (or, but preferably not, convex) relative to the principal longitudinal centerline L. The lines of juncture 30 may comprise those lines or areas where separate flap elements are joined to the main body portion 24. Alternatively, when the flaps 24 are integral with the main body portion 22, the lines of juncture 30 may represent lines of demarcation between the main body portion 22 and the flaps 24 (although it is not necessary that there be a precise line of demarcation).

The flaps 24 can be joined with the main body portion 22 in a number of different manners. Many of the different ways a component (such as the flaps 24) can be "joined to" or "associated with", etc. another component, are set forth in the definitions of these terms contained in U.S. Pat. No. 5,007,906 entitled "Decoupled Sanitary Napkin" which issued to Osborn, et al. on Apr. 16, 1991. When the flaps comprise separate elements, they can be joined to the main body portion 22 by any techniques known to those skilled in the art. Such techniques include, but are not limited to adhesives, heat and/or pressure, ultrasonics, etc.

It is not necessary that the flaps 24 extend from (or be joined along) the longitudinal edges 22a of the main body portion 22. The flaps 24 can joined inward (or "inboard") from the longitudinal edges 22a toward the longitudinal centerline. The flaps 24 can, thus, each be joined to the main body portion 22 along the principal longitudinal centerline L, or along the longitudinal edges 22a of the main body portion 22, or at any place between the principal longitudinal centerline L and the longitudinal edges 22a of the main body portion 22. The flaps 24 will, of course, generally be on opposite sides of the principal longitudinal centerline L.

C. Unitary Release Member

FIGS. 1, 1a and 1b show a preferred embodiment of a sanitary napkin of the present invention. The sanitary napkin 20 of the present invention has at least one unitary release member 57 joined thereto. Preferably, as shown in FIG. 1, the sanitary napkin 20 has two unitary release members 57, one for the flap adhesive 56 of each flap 24.

The overall size and shape of the unitary release member 57 can be readily selected by those skilled in the art. Preferably, the unitary release member 57 is sized and shaped so that it will at least superpose the flap adhesive 56. However, the unitary release member 57 may also be larger than the flap adhesive 56. It is also possible to have one unitary release member 57 for the flap adhesives 56 of both flaps 24. (It should be understood that the size, shape, and orientation of the unitary release member 57 described herein are those of a preferred embodiment. They are not mandatory design features. For example, each flap 24 could comprise a unitary release material 57 which is positioned closer to the distal edge 34 of the flap 24 and a flap adhesive 56 positioned laterally inboard of the unitary release material 57.)

The unitary release member 57 will be any material that will protect the flap adhesive 56 from dirt, keep the flap adhesive 56 form drying out, and keep the flap adhesive 56 from sticking to extraneous surfaces. The unitary release member 57 should also adhere with sufficient tenacity to the flap adhesive to remain in place prior to use, but should be readily removable when the flap 24 is ready to be used. Additionally, the unitary release member 57 is preferably flexible so as not to inhibit the flexibility of the flap 24.

The unitary release member 57 comprises a release material that is joined to at least a portion of the sanitary napkin 20, and may be formed in several different ways. For example, the unitary release member 57 may be formed by securing any commercially available release liner to a portion of the sanitary napkin 20. An example of a suitable release liner is a semi-bleached kraft paper, the adhesive contacting side of which has been silicone treated to provide easy release from the flap adhesive 56. Other examples of suitable release liners are BL 30 MG-A SILOX E1/O and BL 30 MG-A SILOX 4 P/O both of which are manufactured by the Akrosil Corporation. The release liner can be joined to the sanitary napkin 20 by any of the techniques known to those skilled in the art. Such techniques include, but are not limited to adhesives, heat and/or pressure, ultrasonics, etc.

The unitary release member 57 may also be formed by joining an element (e.g., topsheet 40, backsheet 42, flaps 24, etc.) to the sanitary napkin 20, which consists entirely or partially of a material which can act as a suitable release member. Examples of materials which can act as a suitable release member and which can be used to form portions of the sanitary napkin 20, would include woven and nonwoven polyester, polypropylene, nylon, and polyethylene, as well as plastic films, which have been treated with a silicone such as SILOX E1/O, SILOX 4 P/O, SILOX H1A/O, and SILOX H2A/O, all of which are manufactured by the Akrosil Corporation of Menasha, Wis.

Preferably, the unitary release member 57 is formed by treating (e.g., coating, painting, spraying, impregnating, etc.) a portion of the sanitary napkin 20 with a substance, such as silicone, so that the treated portion of the sanitary napkin 20 will function as a suitable release member. Suitable substances for treating portions of the sanitary napkin 20 would include a silicone such as SILOX E1/O, SILOX 4 P/O, SILOX H1A/O, and SILOX H2A/O, all of which are manufactured by the Akrosil Corporation.

Preferably, the unitary release member 57 is formed by spray-coating a portion of the flap 24 with SILOX H2A/O. In a preferred embodiment, the flap 24 will comprise a polyethylene film having a thickness of about 0.001 inch (0.0003 millimeters )

The unitary release member 57 is positioned on the sanitary napkin 20 such that the flap adhesive 56 will overlie the unitary release member 57 when the flap 24 is in a folded configuration. The unitary release member 57 also maintains the flap 24 in a folded configuration until the flap 24 is ready to be used.

Referring to FIGS. 1 and 1a, there is shown a sanitary napkin 20 embodiment of the present invention. The sanitary napkin 20 comprises a main body portion 22 comprising a topsheet 40, a backsheet 42, an absorbent core 44 positioned between the backsheet 42 and the topsheet 40; and a pair of flaps 24 extending from each longitudinal side 22a of the main body portion 22. Each of the flaps 24 comprises a flap adhesive 56 positioned adjacent to the distal edge 34 of the flap 24 and a unitary release member 57 positioned adjacent the proximal edge 32 of the flap 24. The unitary release member 57 is positioned such that it superposes the flap adhesive 56 when the flap 24 is folded along a longitudinally extending fold line 62 as shown in FIG. 1b.

Although the flap adhesive 56 is shown positioned substantially adjacent to the distal edge 34 of the flap 24 in FIG. 1, the flap adhesive 56 may be positioned adjacent to the proximal edge 32 of the flap 24, or anywhere between the distal edge 34 and the proximal edge 32. Additionally, although the flap adhesive 56 is positioned laterally outboard of the unitary release member 57, the unitary release member 57 may be positioned laterally outboard of the flap adhesive 56. However, it is preferred that the flap adhesive 56 be positioned outboard of the unitary release member 57. It is also possible for each flap 24 to have more than one flap adhesive 56 and/or more than one unitary release member 57. However, a single patch of flap adhesive 56 and a single unitary release member 57 for each flap 24 is preferred.

When the user of the sanitary napkin 20 wishes to expose the unitary release member 57 and secure the flap 24 to the underside of the user's undergarment, the user simply pulls the distal edge 34 of the flap 24 thereby unfolding the flap 24 from its folded configuration and simultaneously peeling the flap adhesive 56 from the unitary release member 57. The unitary release material 57 remains joined to the sanitary napkin 20, and does not adversely effect the functionality of the sanitary napkin 20. Preferably, the act of unfolding the flap 24 from its folded configuration and simultaneously peeling the flap adhesive 56 from the unitary release member 57, can be accomplished using only one hand.

The function of the sanitary napkin of the present invention will now be described in greater detail with relation to the wearer's undergarments.

Figure 6:
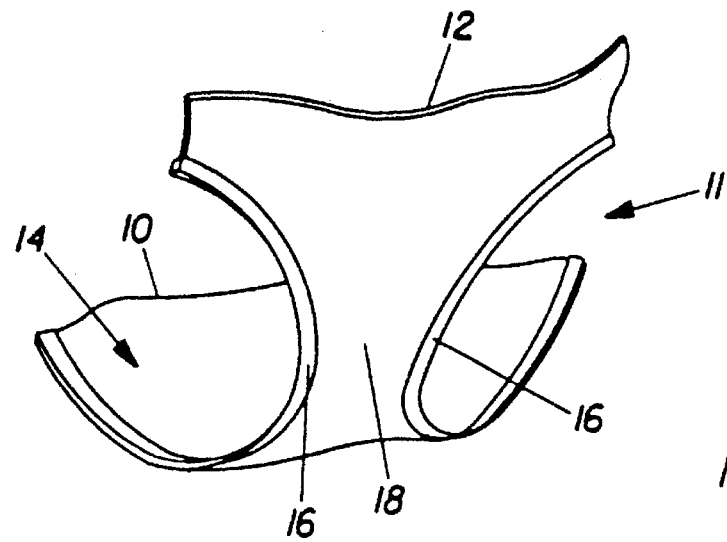
FIG. 6 is a perspective view of the crotch portion of a women's panties.

FIG. 6 is a depiction of the crotch portion 14 of an undergarment 11 of the type commonly worn by many women and well known as a panty. A panty 11 comprises a front section 10, a back section 12, and a crotch portion 14 which joins the front and back sections. The crotch portion 14 comprises two side edges 16 and center crotch portion 18.

Figure 6A:
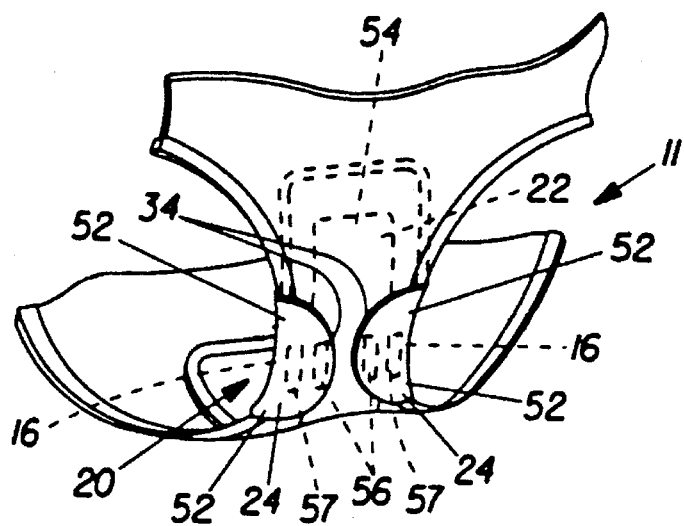
FIG. 6a is the same perspective view of the women's panties shown in FIG. 6 with the sanitary napkin embodiment of the present invention being placed therein for use with the flaps extended and affixed to the underside of the panties.
Figure 6B:
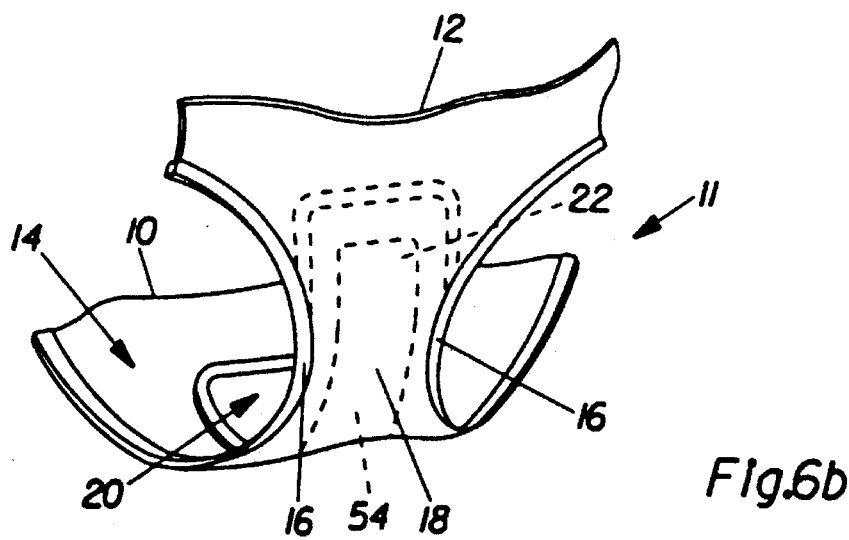
FIG. 6b is the same perspective view of the women's panties shown in FIG. 6 with the a sanitary napkin embodiment of the present invention having tucked flaps, being placed therein for use.

The sanitary napkin 20 of the present invention may be utilized by removing the release liner 58 of the central pad adhesive 54 and placing the sanitary napkin 20 in a panty 11 as shown in FIG. 6b. The center of main body portion 22 is placed in crotch portion 14 of the panty with one end of main body portion 22 extending towards the front section 10 of the panty and the other end towards the back section 12. The backsheet 42 is placed in contact with the inner surface of center crotch portion 18 of the panty. Central pad adhesive 54 maintains main body portion 22 in position. The user grasps and pulls the distal edge 34 of the flap 24, thereby peeling the flap adhesive 56 from the the unitary release member 57. The distal portions of flaps 24 are then folded around the side edges 16 of the panty. The flap adhesives 56 secure the flaps 24 to the underside of the panty as shown in FIG. 6a. The unitary release members 57 remain joined to the flap 24, but do not adversely effect the functionality of the sanitary napkin 20.

Although the unitary release member 57 is shown in FIGS. 1–1b as being joined to a portion of the flap 24, it is not necessary that the unitary release member 57 be secured to a portion of the flap 24. The unitary release member 57 may be joined to the flap 24, main body portion 22, or any other portion of the sanitary napkin 20. An example of a sanitary napkin embodiment of the present invention having an unitary release member 57 joined to the main body portion 22, is shown in FIGS. 5–5b.

Figure 5A:
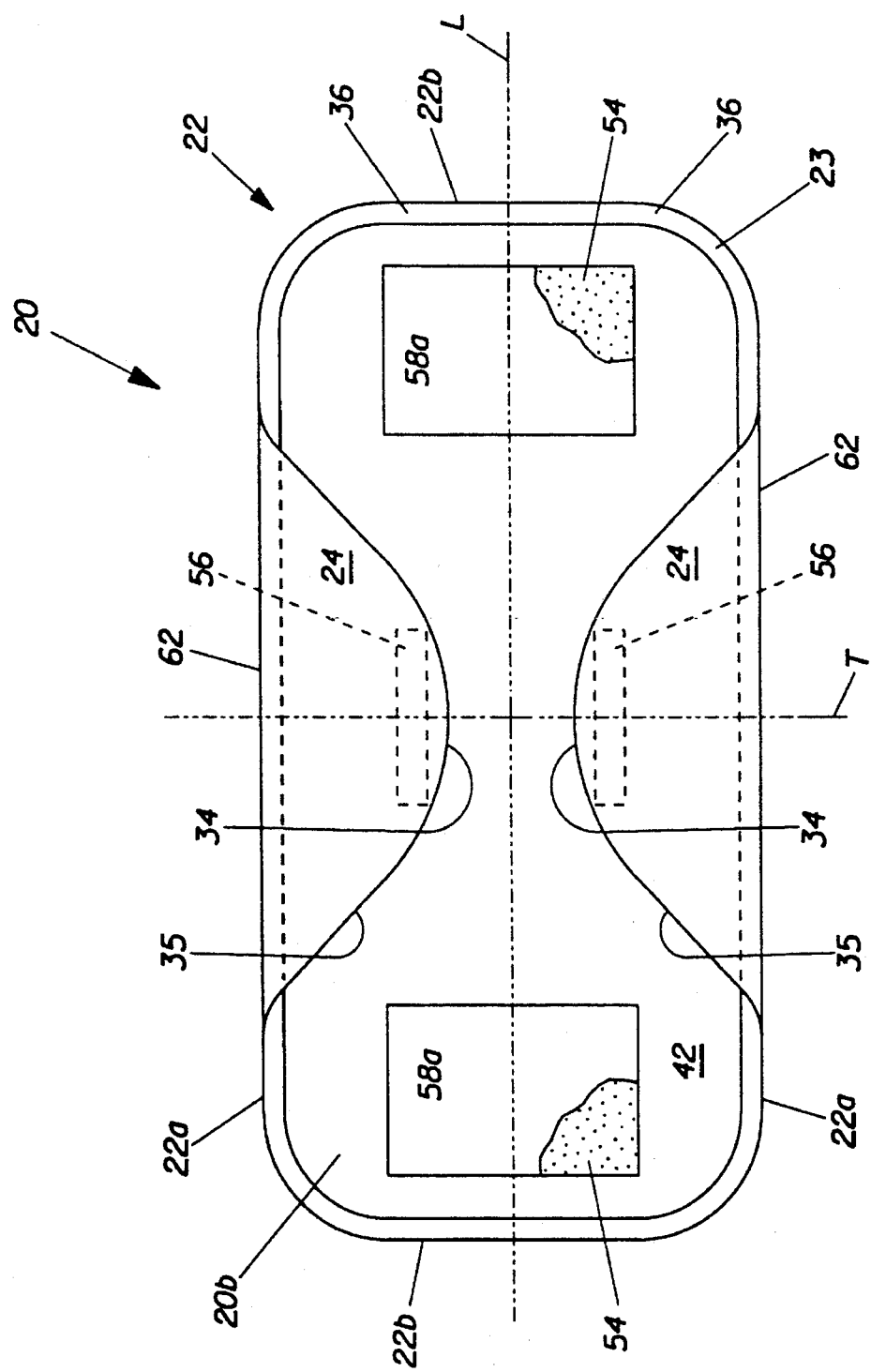
FIG. 5a is a plan view of the sanitary napkin of FIG. 5 having the flaps folded over the garment side of the main body such that the flap adhesives superpose the unitary release material.
Figure 5:
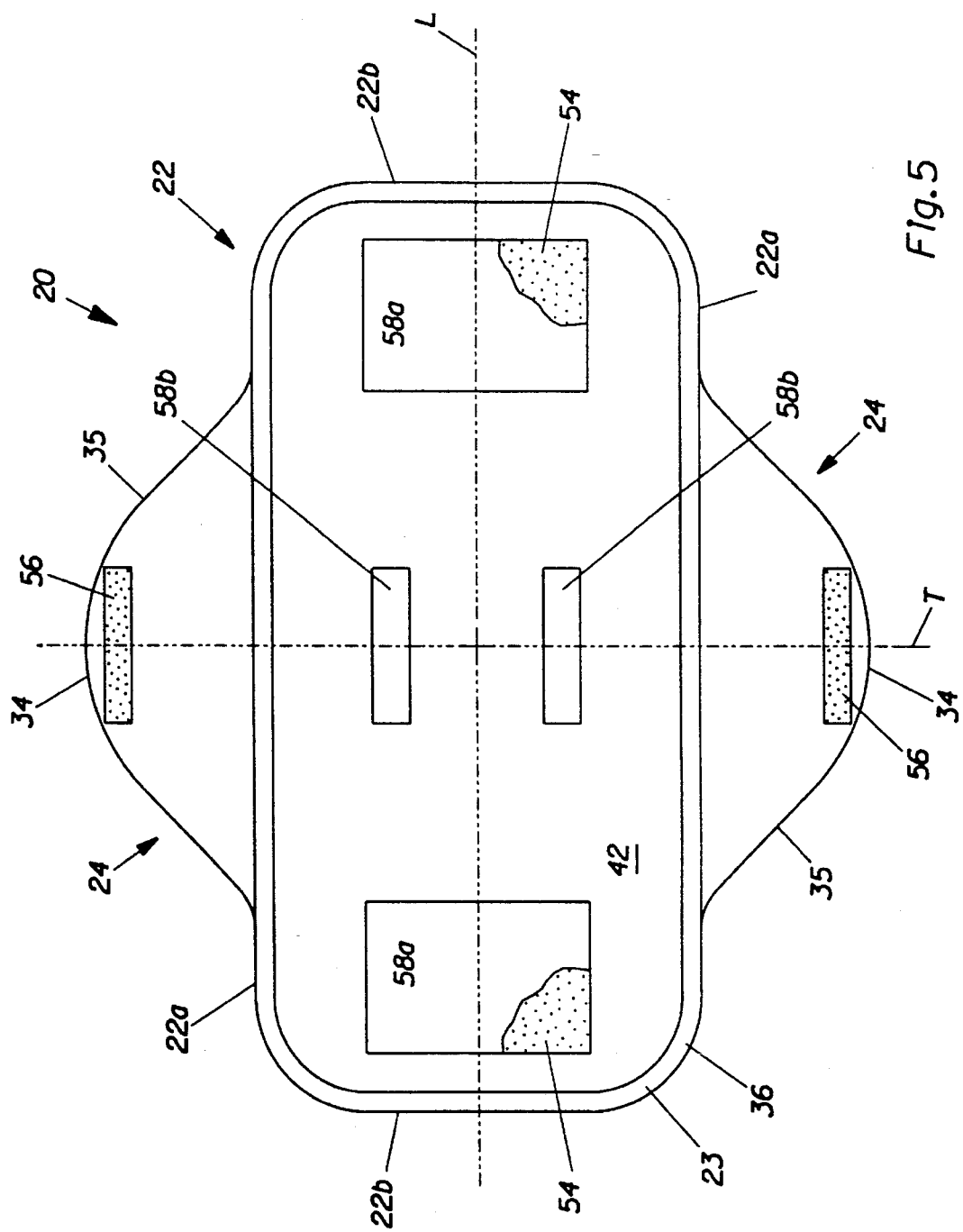
FIG. 5 is a plan view of an alternate sanitary napkin embodiment of the present invention having the garment side facing the viewer, and having portions cut-away to show the underlying structures.

Referring to FIG. 5–5b, there is shown an alternate sanitary napkin 20 embodiment of the present invention. The sanitary napkin 20 comprises a main body portion comprising a topsheet 40, a backsheet 42, an absorbent core 44 positioned between the topsheet 40 and the backsheet 42; and a pair of flaps 24 extending from each longitudinal edge 22a of the main body portion 22. Each of the flaps 24 comprises a flap adhesive 56 positioned adjacent to the distal edge 34 of the flap 24.

The sanitary napkin 20 of FIG. 5 comprises an unitary release member 57 positioned on the garment side 20b of the main body portion 22. The unitary release member 57 is shown positioned between the longitudinal centerline L and the longitudinal edges 22a of the main body portion 22. The unitary release member 57 is positioned such that it superposes the flap adhesive 56 when the flap 24 is folded along a longitudinally extending fold line 62, and maintains the flaps 24 in their folded configuration, as shown in FIG. 5a.

The central pad adhesive 54 comprises two discrete patches of pressure sensitive adhesive disposed at opposite ends of the main body portion 22. Because of the configuration and arrangement of the central pad adhesive 54 and the flaps 24, the flaps 24 do not interfere with or obstruct the central pad adhesive 54. Therefore, the flaps 24 may or may not be used while the sanitary napkin is being used, and will not adversely effect the functionality of the sanitary napkin 20, i.e., will not obstruct the absorbency of the body-facing side 20a and will not obstruct the central pad adhesive 54 of the garment side 20b.

Although the central pad adhesive 54 is shown as two discrete patches positioned substantially adjacent opposite transverse edges 22b of the main body portion 22, the central pad adhesive 54 may be arranged in other configurations which provide the same result. For example, the central pad adhesive 54 may be generally rectangular in shape and extend along the longitudinal centerline between the distal edges 34 of the flaps 24 in their folded configuration. Alternatively, the central pad adhesive 54 may have a generally hourglass shape and be positioned on the garment side 20b of the main body portion 22 such that the edges of the central pad adhesive 54 are substantially adjacent the edges 35 of the flaps 24 and the transverse edges 22b of the main body portion 22. The particular size and shape of the central pad adhesive 54 can be readily selected by those skilled in the art.

A sanitary napkin having flaps and having a release surface disposed on the undergarment-facing side of the sanitary napkin is disclosed in E.P.O. Publication 0 471 587,A1 which claims priority from U.S. patent application Ser. No. 568,937, filed Aug. 17, 1990. Both of these patent applications are incorporated herein by reference.

Figure 7:
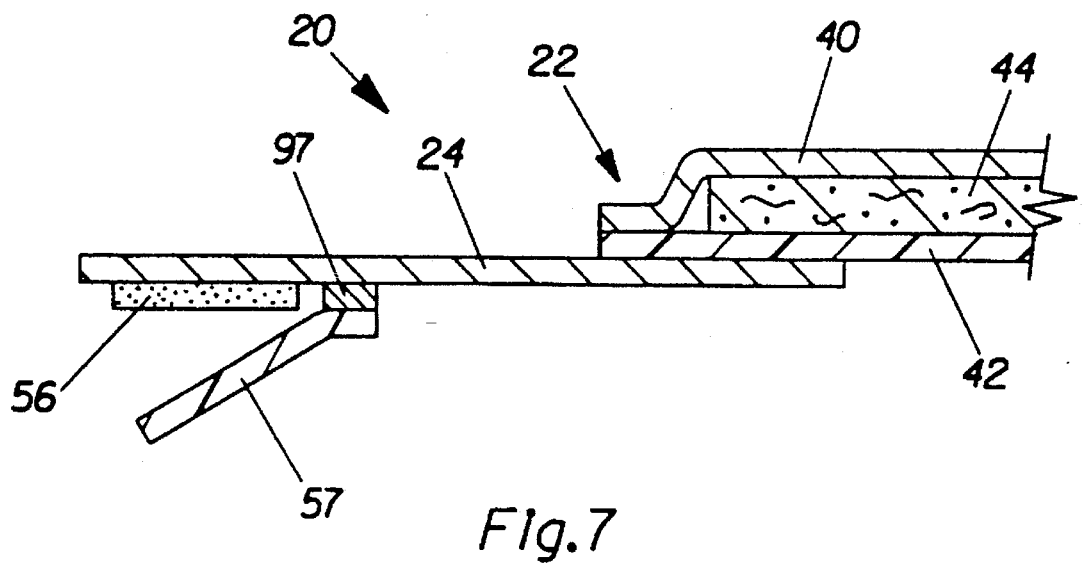
FIG. 7 is a transverse cross-sectional view of a portion of an alternate embodiment of the present invention, showing one of the flaps and part of the main body portion.

In an alternate embodiment, the sanitary napkin 20 may have a unitary release member 57 that can be removably secured to the flap adhesive 56 without the flap 24 being folded onto itself or the main body portion 22. FIG. 7 is a lateral cross-sectional view of a portion of a sanitary napkin 20 showing one of the flaps 24 and a portion of the main body portion 22. In this embodiment, a portion of the unitary release member 57 is joined to the flap 24 at bond area 97. When the unitary release member is peeled from the flap adhesive 56, it remains attached to the flap 24 at the bond area 97 so the user does not need to further handle or dispose of the release material. The bond area 97 may be a single discrete spot bond, group of spot bonds, a solid line of bonding or a segmented line of bonding. The bond area 97 may be located laterally inboard or outboard, or longitudinally forward or behind the flap adhesive 56.

Figure 7A:
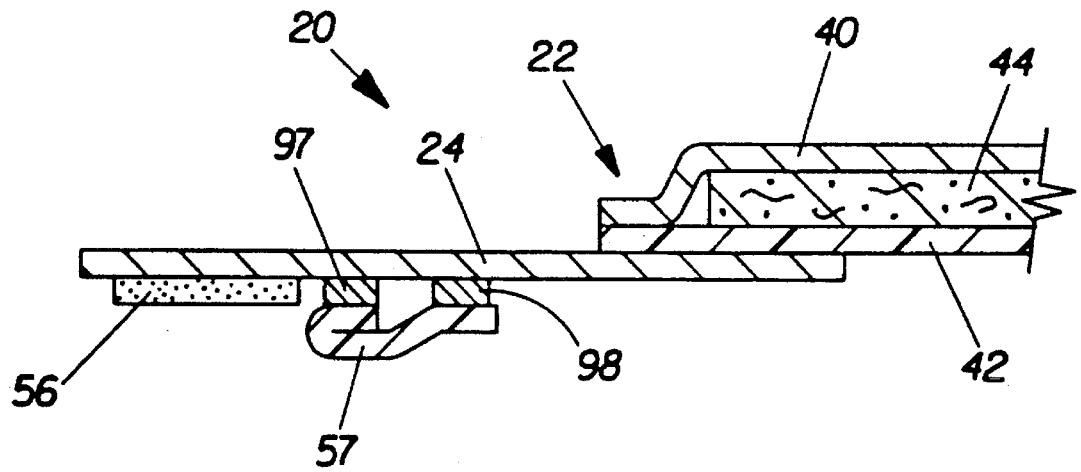
FIG. 7a is a transverse cross-sectional view of a portion of another alternate embodiment of the present invention, showing one of the flaps and part of the main body portion.

A further alternate embodiment is shown in FIG. 7a. After peeling the unitary release member 57 from the flap adhesive 56, the user would reattach the loose end of the unitary release member 57 to the flap 24 with a bonding material 98. This prevents the loose end of the unitary release member 57 from moving freely and potentially interfering with the application of the flap 24. Bonding material 98 could be originally located on either the back of the unitary release member 57, in the flap 24 or be a cohesive material originally located on both the unitary release member 57 and the flap 24.

C. Sanitary Napkins Having Tucked Flaps and a Unitary Release Member

Figure 2:
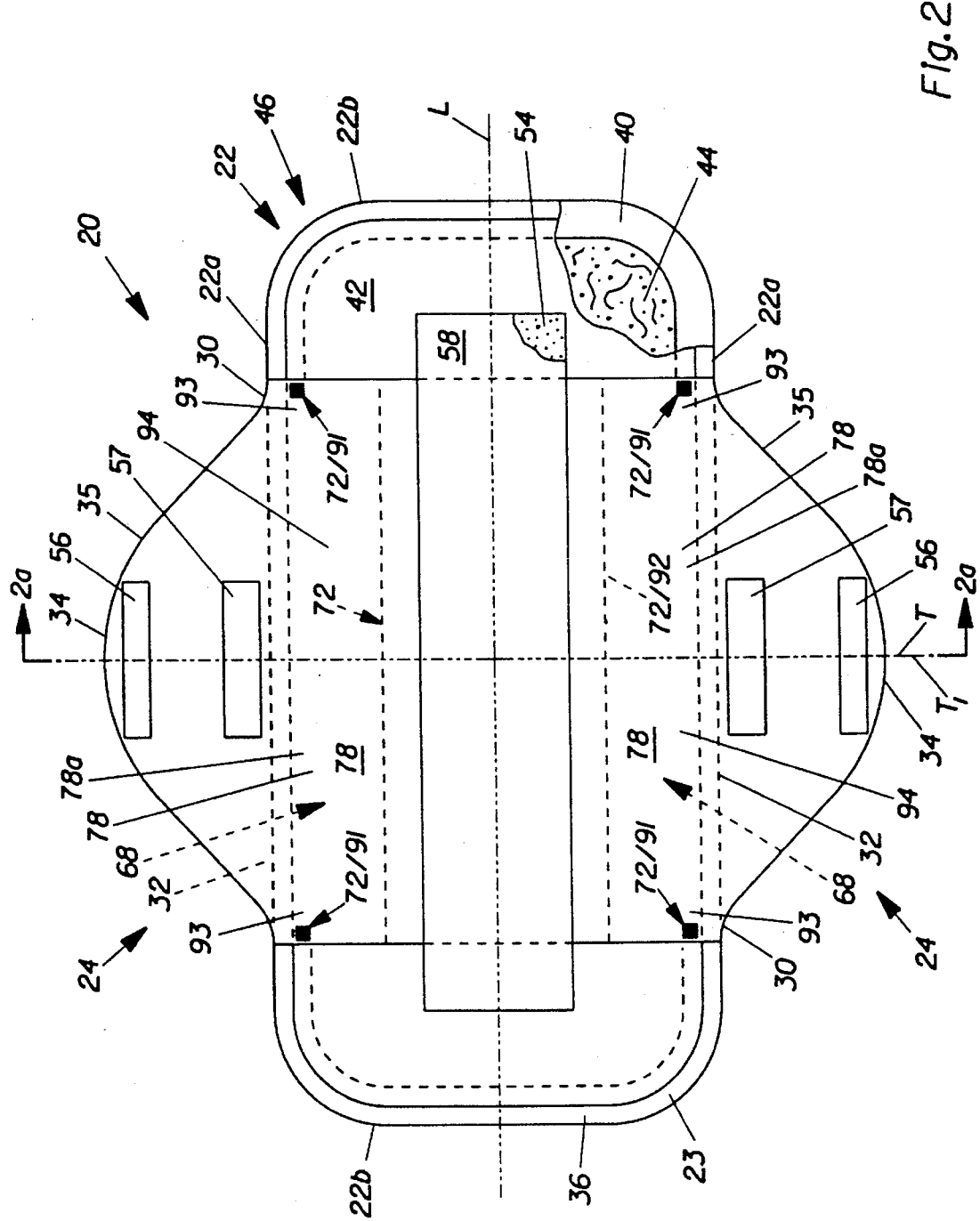
FIG. 2 is a plan view of an alternate sanitary napkin embodiment of the present invention having portions cutaway to show the absorbent core.
Figure 2A:
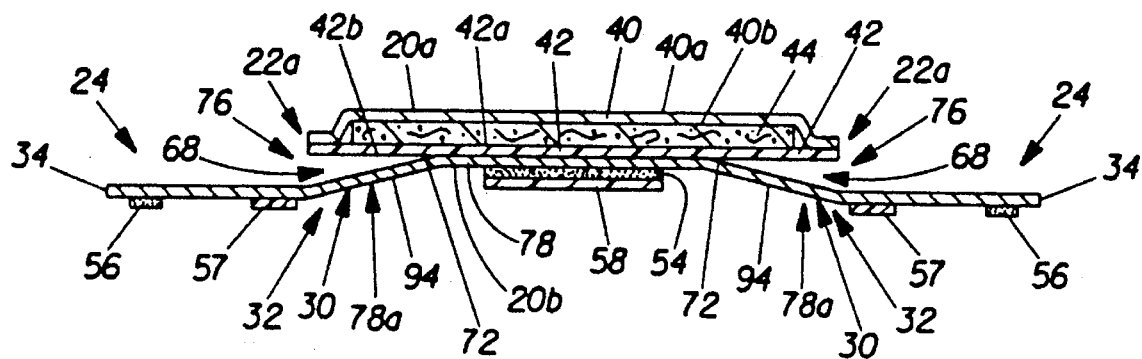
Figure 2B:
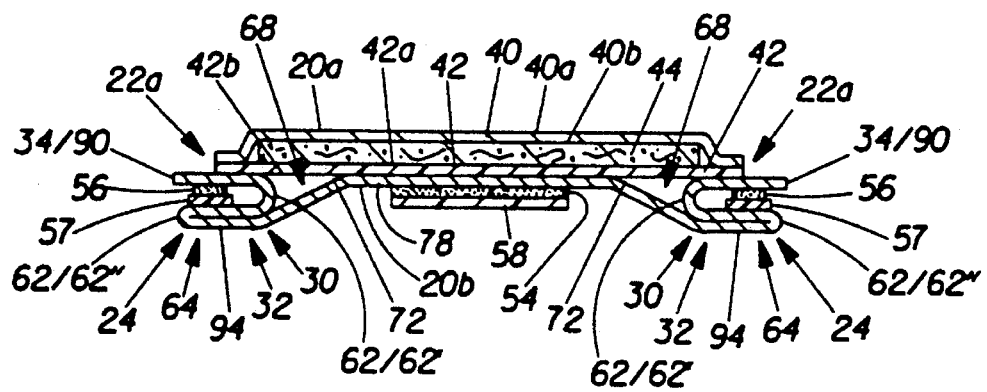
FIG. 2b is a cross-sectional view of the sanitary napkin of FIG. 2a showing the flaps tucked into the recessed areas in a folded configuration with the unitary release material superposing the flap adhesives.

In the most preferred case (as will be subsequently described in greater detail), the sanitary napkin will have the flaps tucked into a recessed area and will have at least one zone of differential extensibility. However, it is also possible to have a sanitary of the present invention with the flaps tucked into a recessed area without having zones of differential extensibility. FIGS. 2, 2a, and 2b show a preferred embodiment of a sanitary napkin 20 of the present invention having a unitary release member 57 and a recessed area 68 for receiving the flaps 24.

As used herein the terms "optional flaps" or "tucked flaps" shall refer to the flaps of an absorbent article, which are tucked or are capable of being tucked into a recessed area 68. A flap is capable of being tucked into a recessed area if it is joined to the sanitary napkin such that at least a portion of the flap may be positioned between the decoupled portion of a retaining member and the absorbent assembly of the main body portion. Referring to FIG. 2, the sanitary napkin 20 basically comprises a main body portion 22 and two flaps 24 (shown in the extended position) joined to the main body portion 22. The main body portion 22 comprises an absorbent means represented by an absorbent assembly 46 and two retaining members 78 joined to the absorbent assembly 46.

The retaining member 78 comprises a pair of end regions 93 and a center region 94 positioned between and joined to the end regions 93. At least a portion of the end regions 93 are joined to the absorbent assembly 46. At least a portion of the center region 94 is detached or decoupled from the absorbent assembly 46. The area between the decoupled center region 94 and the absorbent assembly 46, forms a recessed area 68 wherein a portion of at least one of the flaps 24 may be tucked. The end regions 93 are each joined to the absorbent assembly 46 at a point of connection 72. As used herein, the term "point of connection" refers to regions where the retaining member 78 is joined to the absorbent assembly 46 of the main body portion 22. These regions can be of any shape or configuration, but they are not limited to spots or points. Thus, these regions can comprise flanges, strips, intermittent lines, spots, and the like.

The absorbent assembly 46 preferably comprises a liquid pervious topsheet 40, a liquid impervious backsheet 42 joined to the topsheet 40, and an absorbent core 44 positioned between the topsheet 40 and the backsheet 42.

The sanitary napkin 20 comprises two recessed areas in which the flaps 24 may be tucked. Each recessed area 68 is formed between the decoupled portion of the center region 94 of the retaining member 78 and the absorbent assembly 46 of the main body portion 22. Each recessed area 68 has a mouth 76. The mouth 76 is formed between the longitudinal edge 78a of the decoupled portion of the retaining member 78 and the absorbent assembly 46 of the main body portion 22.

The retaining member 78 can be joined to the absorbent assembly 46 of the main body portion 22 in a number of different manners. Many of the different ways a component (such as the retaining member 78) can be "joined to" or "associated with", etc. another component are set forth in the definitions of these terms contained in U.S. Pat. No. 5,007,906 entitled "Decoupled Sanitary Napkin" which issued to Osborn, et al. on Apr. 16, 1991. When the retaining member is comprised of an element discrete from the absorbent assembly 46, i.e. is not integral with the topsheet, backsheet, etc, it can be joined to the absorbent assembly 46 by any techniques known to those skilled in the art. Such techniques include, but are not limited to adhesives, heat and/or pressure, ultrasonics, etc. The point of connection 72 may comprise flanges, strips, intermittent lines, spots, and the like, or may comprise combinations of flanges, strips, intermittent lines, spots, and the like. Therefore, the point of connection 72 may be a line which is concave, straight, or convex and may form any angle relative to the principal longitudinal centerline L.

The retaining members 78 can each be joined to the absorbent assembly 46 of the main body portion 22 along the principal longitudinal centerline L, or along the longitudinal edges 46a of the absorbent assembly 46, or at any place between the principal longitudinal centerline L and the longitudinal edges 46a of the absorbent assembly 46. The retaining members 78 will, of course, generally be on opposite sides of the principal longitudinal centerline L.

The retaining member 78 is generally longitudinally oriented on the absorbent assembly 46. The retaining member is longitudinally oriented on the absorbent assembly 46 when the longitudinal edge 78a of the retaining member 78 is oriented in a direction substantially parallel to the principal longitudinal centerline L or in a direction having a vector component substantially parallel to the prinicpal longitudinal centerline L.

The retaining member 78 is generally compliant soft feeling and non-irritating to the users skin. The retaining member 78 is preferably made from any of the materials conventionally used for sanitary napkins 20. Examples of suitable materials that can be used for the retaining member 78 are woven and nonwoven polyester, polypropylene, nylon, and polyethylene, as well as plastic films. The retaining member 78 may be comprised of one or more of the elements of the absorbent assembly 46, e.g., topsheet 40, backsheet 42, etc. Preferably, the retaining member 78 will comprise a piece of material discrete from the topsheet, backsheet, etc.

The overall size and shape of the retaining members 78 may be readily selected by those skilled in the art and will be dependent upon the desired size and shape of the recessed area 68 and the size and shape of the flaps 24 as they are tucked into the recessed area 68. Although it is not necessary that the retaining members 78 be mirror images of each other, it is preferred that the retaining members 78 are mirror images of each another. Whether or not the retaining members 78 are symmetrical about the principal transverse centerline T is also dependent upon the desired size and shape of the recessed area 68, as well as the location and symmetry of the flaps 24. However, it should be understood that the retaining members 78 need not have a shape, size, or location which exactly corresponds to the size, shape, and location of the flaps 24. It is only required that the retaining members 78 be sized, shaped, and positioned such that the retaining member 78 forms a recessed area 68 which can accommodate the flap 24 in a tucked configuration.

It is not necessary that both retaining members 78 be formed of a single piece of material as shown in FIGS. 2–2b. Each retaining member 78 may each be formed from a separate piece of material. It is also not necessary that the retaining members 78 be joined to the backsheet 42 of the absorbent assembly 46. The retaining members 78 may be joined to any element of the absorbent assembly 46. Many various configurations which provide a recessed area 68 between the retaining member 78 and the absorbent assembly 46 of the main body portion 22 of the sanitary napkin 20, will be readily apparent to those skilled in the art.

Referring to FIGS. 2–2b, the sanitary napkin 20 has two recessed areas 68, one on each side of the principal longitudinal centerline L. It can be seen from FIGS. 2a and 2b that the flaps 24 are integral with the retaining members 78. The point of connection 72 of each retaining member 78 comprises a combination of a straight line bond 92 and two spot bonds 91. The line bond 92 joins a portion of the center region 94 of the retaining member 78 to the absorbent assembly 46. The two spot bonds 91 join a portion of the end regions to the absorbent assembly 46. The portion of the center region 94 which is decoupled from the absorbent assembly 46 of the main body portion 22 forms the recessed area 68. Although the spot bonds 91 are shown in FIG. 2 as being positioned adjacent to the longitudinal edge 22a of the main body portion 22, the spot bonds 91 may be positioned anywhere between the longitudinal edge 22a of the main body portion 22 and the principal longitudinal centerline L.

FIG. 2b is a lateral cross-sectional view of the sanitary napkin 20 of FIG. 2a showing the flaps 24 tucked into the recessed areas 68 in a folded configuration. Each flap 24 of the sanitary napkin 20 has a first longitudinal fold 62' which is made upward toward the absorbent assembly 46 and a second fold 62" which is again made upward toward the absorbent assembly 46. This forms a tucked flap 24 which is configured in an S-fold. This configuration allows the distal edge 34 of the flap 24 to form a graspable tab member 90.

Preferably each tucked flap 24 will be provided with a graspable tab member 90. As used herein, the term "tab member" will refer to an element or component of the sanitary napkin 20 which protrudes form the recessed area 68 and may be used to remove the flap 24 from the recessed area 68. The graspable tab member 90 may extend laterally beyond the longitudinal edge of the absorbent assembly 46 or may extend laterally beyond the longitudinal edge 78a of the retaining member 78. Preferably, the graspable tab member 90 extends laterally beyond the longitudinal edges of both the absorbent assembly 46 and the retaining member 78. The graspable tab member 90 preferably extends from the recessed area 68 at least between about 2 millimeters to about 5 millimeters. More preferably, the tab member 90 extends from the recessed area 68 between about 5 millimeters to about 10 millimeters. A preferred tab member 90 is formed by folding, pleating, or corrugating the flap 24 such that the distal edge 34 of the flap 24 protrudes from the mouth 76 of the recessed area 68. There are many different fold configurations which will result in the distal edge 34 of the flap 24 protruding from the mouth 76 of the recessed area 68. An example of particularly preferred fold configurations which results in the distal edge of the flap 24 forming a tab member 90, are shown in FIGS. 2b, 3b. Other suitable fold configurations will be readily apparent to those skilled in the art.

Sanitary napkins having tucked flaps 24 and various methods for forming the recessed areas 68, are discussed in greater detail in the commonly-assigned, co-pending, U.S. patent application Ser. No. 07/906,629, "Absorbent Article Having Tucked Flaps", filed Jun. 30, 1992, in the name of Thomas W. Osborn, III and Bruce W. Lavash, which patent application is filed concurrently herewith and is incorporated herein by reference.

The flap 24 comprises a flap adhesive 56 and an unitary release member 57 joined thereto. The flap adhesive 56 is positioned substantially adjacent to the distal edge 34 of the flap 24. The unitary release member 57 is positioned on the garment side 20b of the flap 24 between the distal edge 34 and the proximal edge 32 of the flap 24. To tuck the flap 24 into the recessed area 68, the flap 24 is folded along a first longitudinally extending fold line (referred to in FIG. 2b as fold line 62') such that the flap adhesive 56 overlies and is removably secured to the unitary release member 57. The flap 24 is then folded along a second longitudinally extending fold line (referred to in FIG. 2b as fold line 62") such that the first fold line 62' is positioned within the recessed area 68. Preferably, the distal edge 34 of the flap 24 extends from the mouth 76 to form a graspable tab member 90.

The sanitary napkin 20 of FIGS. 2–2b may be utilized by removing the release liner 58 of the central pad adhesive 54 and placing the sanitary napkin 20 in a panty 11 as shown in FIG. 6. The center of main body portion 22 is placed in crotch portion 14 of the panty with one end of the main body portion 22 extending towards the front section 10 of the panty and the other end towards the back section 12. The backsheet 42 is placed in contact with the inner surface of the center crotch portion 18 of the panty. The central pad adhesive 54 maintains the main body portion 22 in position. The flaps 24 remain positioned in the recessed areas 68. The panty is pulled up into position on the wearer's lower torso. Although the flaps 24 have not been used and remain tucked into the recessed areas 68, the flaps 24 will not adversely affect the functionality of the sanitary napkin 20.

Alternatively, the sanitary napkin 20 of FIGS. 2–2b may be utilized by removing the release liner 58 from the central pad adhesive 54 and placing the sanitary napkin 20 in the panty 11 with one end of the main body portion 22 extending towards the front section 10 of the panty and the other end of the main body portion 22 extending towards the back section 12. The user may then grasp the tab member 90 to draw the flap 24 from the recessed area 68 and simultaneously peel the flap adhesive from the unitary release member 57. The distal edges 34 of the flaps 24 are folded around the side edges 16 of the panty, and the flap adhesives 56 are secured to the underside of the panty as shown in FIG. 6a. The panty is then pulled up into position on the wearer's lower torso.

E. Sanitary Napkin Having Flaps With Zones of Differential Extensibility and a Unitary Release Member In the most preferred case the sanitary napkin will have at least one zone of differential extensibility (or "zone of extensibility", or simply "zone") 50. Preferably, as shown in FIG. 3, the sanitary napkin 20 has four zones of differential extensibility 50, one in each quarter of the sanitary napkin 20. The zones of differential extensibility 50 are preferably located along a portion of the fold line where the flaps 24 are folded around the wearer's panty crotch. The fold line will typically be located along or adjacent the longitudinal juncture 30 of each flap 24. Since the terms "portions", "zones", and "regions", as used herein, refer to general areas, the zones of differential extensibility 50 and the corner regions 52 are, thus, not limited to points which lie precisely on the lines of juncture 30. Typically, they will include both those points which lie on the lines of juncture 30 as well as the surrounding areas of the sanitary napkin 20 (which include the aforementioned fold lines). The longitudinal junctures, thus, typically serve as good approximations for the location of the zones of differential extensibility 50.

The corner regions 52 are designated as such because they typically include the "corners" formed along the periphery 23 of the main body portion of sanitary napkin 20. The "corners" occur where the edges 35 of the flaps 24 intersect with the longitudinal side edges 22a of the main body portion 22 when the sanitary napkin 20 is shown in a plan view. It is not necessary for there to be a sharp angle formed at the intersection of these edges, or for lines of demarcation to designate the same, however. (Another way to describe the corner regions 52 is with reference to U.S. Pat. No. 4,917,697 issued to Osborn, III, et al. The corner regions 52 described herein are typically comprised at least of those areas shown as having slits or notches in the Osborn, et al. patent. (For simplicity, these areas may be referred to herein as "notch regions"). However, the corner regions 52 in the present invention preferably encompass a larger area than the slits or notches shown in the Osborn patent.)

The portions of the flaps 24 in the corner regions 52 of the sanitary napkin 20 may be referred to as the "corner regions of the flaps" or "flap corner regions". These may be separately designated 52' although they are still considered to comprise the corner regions 52, per se.

Figure 3A:
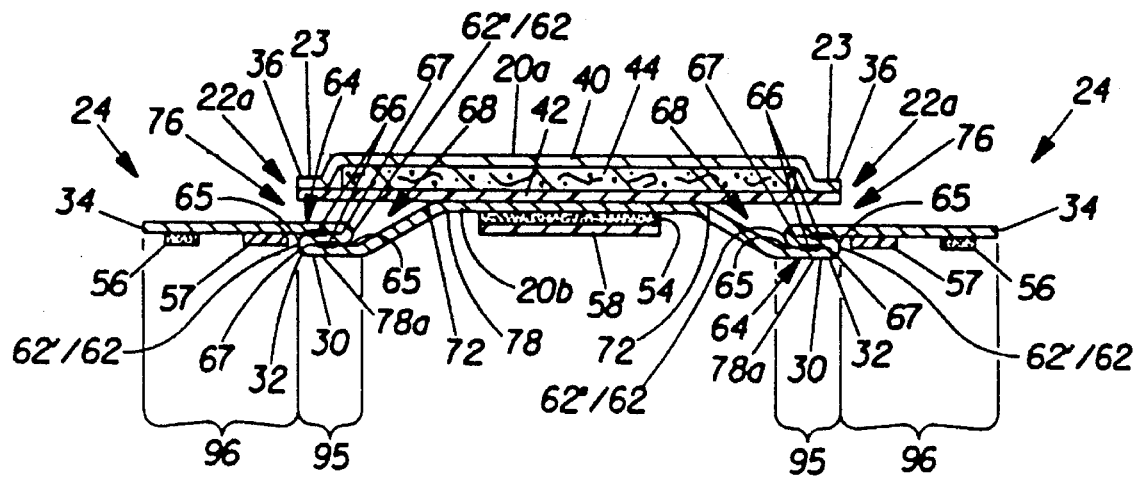
FIG. 3a is a transverse cross-sectional view of the sanitary napkin of FIG. 3.
Figure 3B:
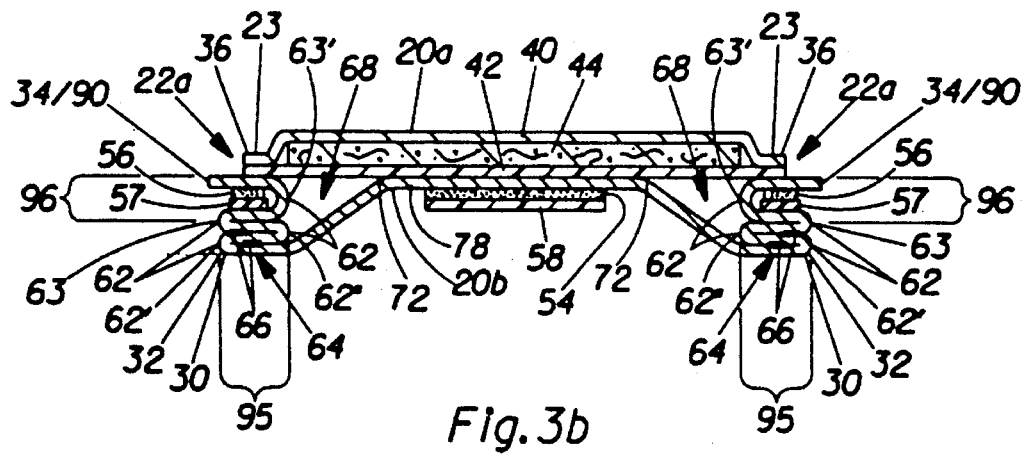
FIG. 3b is a cross-sectional view of the sanitary napkin of FIG. 3 showing the flaps tucked into the recessed areas in a folded configuration with the unitary release material superposing the flap adhesives.

FIGS. 3, 3a, and 3b show an embodiment of the present invention which has one preferred type of zones of differential extensibility 50. In the embodiment shown in FIGS. 3, 3a, and 3b the zones of differential extensibility 50 comprise portions of the sanitary napkin 20 that have slack provided therein. These portions of the sanitary napkin 20 comprise at least the flap corner regions 52'.

The slack is provided to the sanitary napkin 20 in the embodiment shown in FIGS. 3, 3a, and 3b by pleating and then gathering in portions of the flaps. The flaps 24 are pleated or folded with generally longitudinally-oriented fold lines 62. The fold lines 62 can run along and/or outboard (or even inboard) of the juncture 30 of the flaps and the main body portion 22. The pleated sections of the flaps (the "pleats") 64 are preferably folded on top of each other (that is, stacked perpendicular to the plane of the sanitary napkin). In alternative embodiments, they may be folded and arranged side-by-side. The pleated sections are gathered in or restrained from opening by a flap pleat restraint 66 located along the flap transverse centerline $T_1$. This provides the sanitary napkin, and particularly the flaps 24, with corner regions which are extensible in the transverse direction and with center portions 27 (along the flap transverse centerline $T_1$) which are not.

The zones of differential extensibility 50 are most preferably located at those points where the edges 35 of the flaps 24 intersect the edges 16 of the panty when the sanitary napkin 20 is worn.

The total area covered by the zones of differential extensibility 50 can vary widely. The area can cover a relatively large portion of the sanitary napkin, provided there remain some portions of the sanitary napkin adjacent at least portions of the principal longitudinal centerline and the flap transverse centerline that are less extensible. The zones of differential extensibility 50 can be provided along the entire juncture 30 of the flaps 24 with the main body portion 22. In alternative embodiments, the zones of differential extensibility 50 can be provided throughout the entire flap (for instance, if the entire flap is pleated with longitudinally-oriented pleats).

Again referring to FIGS. 3, 3a, and 3b, the flaps 24 are pleated or folded with generally longitudinally-oriented fold lines 62. The pleated sections are gathered in or restrained from opening by a flap pleat restraint 66 located along the flap transverse centerline $T_1$. This provides the sanitary napkin, and particularly the flaps 24, with corner regions which are extensible in the transverse direction and with center portions 27 (along the flap transverse centerline $T_1$) which are not.

In such a pleated embodiment, the flaps 24 can be provided with any number of fold lines. For instance, in the most basic form of the pleated embodiment, the flaps can simply be folded inward toward the principal longitudinal centerline L along a single line along the juncture 30 and tacked to the main body portion 22, the restraining member 78, or the flap itself, at a point inboard of the juncture 30 (which is preferably in the area of the flap transverse centerline $T_1$). Typically, however, as shown in FIG. 3a, the flaps will have at least two pleat fold lines 62.

The flap pleat restraint 66 can be any suitable type of element capable of keeping a portion of the pleated material from unfolding. The flap pleat restraint 66 can be located along the flap transverse centerline $T_1$, or it can be spaced some distance away from the flap transverse centerline $T_1$. The flap pleat restraint 66 is, however, preferably located at some place along the flap transverse centerline $T_1$. This creates flaps with pleats which are able to open up an equal amount in both the front and back halves 26 and 28 for a preferred fit around the panty crotch. The flap pleat restraint 66 is also preferably located more toward the mouth 65 of the fold as opposed to the crease 67 of the fold as shown in FIG. 3. The amount of differential extensibility of the flap will increase as the flap pleat restraint 66 is positioned close to the mouth 65 of the fold. The flaps 24 can have two flap pleat restraints 66, one located along (or spaced some distance away from) the flap transverse centerline $T_1$ for each flap, or they can have a single flap pleat restraint that spans from one flap to the other.

The flap pleat restraints 66 shown in FIG. 3a are "interior" restraints, i.e., they are located in between two pleated or folded sections 64 of the flaps 24. In alternative embodiments, the flap pleat restraint 66 can be of a type which secures the pleated sections 64 of the flaps 24 from outside (or exterior) of the pleated sections.

The flap pleat restraint 66 can be of any suitable construction. Suitable flap pleat restraints 66 include, but are not limited to adhesives, ultrasonic bonds, heat and/or pressure bonds, tapes, etc. These different types of flap pleat restraints can be in an unlimited number of configurations. Such configurations can include spots, lines, patches, etc.

FIG. 3 shows an embodiment of the present invention having two recessed areas 68, one on each side of the principal longitudinal centerline L, and having four zones of differential extensibility, one in each quarter of the sanitary napkin 20. The zones of differential extensibility 50 are formed by folding the flaps 24 to form a pleat and securing each fold of the pleat along the principal transverse centerline T, using a flap pleat restraint 66.

Each of the flaps 24 of the sanitary napkin 20 of FIG. 3, is joined along a line of juncture 30 to the retaining member 78. The retaining member 78 is joined to the sanitary napkin 20 along lines of connection 72 to form the recessed areas 68. The line of juncture 30 of the flap 24 is represented by a line of demarcation between the flaps 24 and the retaining member 78. Although there is not a precise line of demarcation between the retaining member 78 and the flap 24, the line of juncture 30 for each flap 24 is located generally between the line of connection 72 of the retaining member 78 and that portion of the flap 24 which generally corresponds with the longitudinal edge 22a of the main body portion 22 when the flap 24 is extended out in an unfolded, unpleated configuration.

It is not necessary for the flaps 24 to be joined to the retaining member 78, and it should be understood that the flaps 24 may be joined to the topsheet 40, backsheet 42, or both, or may be joined to any other element of the sanitary napkin 20. However, in the preferred embodiments of the present invention, the flaps 24 will be joined to the retaining member 78. In the most preferred embodiment the flaps 24 will be integral with and extensions of the retaining member 78.

Referring to FIG. 3a and 3b, each flap 24 of this embodiment has a first portion 95 and a second portion 96. The first portion 95 comprises a pleat 64 which is secured by flap pleat restraints 66. The second portion 96 comprises the flap adhesive 56 and the unitary release material 57.

The first portion 95 of each flap 24 has two fold lines 62 that form the pleat 64. The first fold that forms the pleat 64 is made inward toward the garment side 20b of the sanitary napkin 20. The second fold that forms the pleat 64 is also made inward towards the garment side 20b of the sanitary napkin 20. The fold line 62 that is closest to the proximal edge 32 of the flap 24 when the first portion 95 is unfolded, comprises a first pleat-forming fold line 62'. The fold line 62 that is located farther away from the proximal edge 32 of the flap 24 when the first portion 95 is unfolded, comprises a second pleat-forming fold line 62".

The pleat 64 of the first portion 95 of the flap 24, is positioned inboard of the longitudinal edge 22a of the main body portion 22 when the sanitary napkin 20 is looked at from a top plan view such as in FIG. 3. This results in the pleat 64 of the first portion 95 being positioned in the recessed area 68 between the retaining member 78 and the backsheet 42 of the main body portion 22 when the flap 24 is extended as shown in FIG. 3a or when the flap is tucked as shown in FIG. 3b.

Again referring to FIGS. 3, 3a, and 3b, the second portion 96 of each flap 24 comprises a flap adhesive 56 and an unitary release member 57. The flap adhesive 56 is positioned adjacent to the distal edge 34 of the flap 24 and the unitary release member 57 is positioned adjacent to the first portion 95 of the flap 24, such that when the second portion 96 is folded along a longitudinally extending fold line 62, the flap adhesive 56 will superpose the unitary release member 57 and be removably secured thereto.

When the flap 24 is tucked into the recessed area 68 as shown in FIG. 3b, the second portion 96 will comprise two longitudinally extending fold lines 62. The fold line 62 located closest to the first portion 95 when the second portion is unfolded, comprises a first tuck-forming fold line 63. The fold line located farther away from the first portion of the flap 24 when the second portion is unfolded, comprises a second tuck-forming fold line 63'. The first tuck-forming fold line 63 is formed by folding the flap material of the second portion 96 towards the garment side 42b of the backsheet 42. The second tuck-forming fold line 63' is formed by folding the flap material of the second portion 96 toward the garment side 42b of the backsheet 42 and brings the flap adhesive 56 in face to face relation with the unitary release member 57 such that the flap adhesive is removably secured thereto. This results in the second portion 96 of the flap 24 being configured in an S-fold and being positioned in the recessed area 68 between the first portion 95 of the flap 24 and the backsheet 42 of the main body portion 22 with the distal edge 34 of the flap 24 being positioned at or near the mouth 76 of the recessed area 68. Preferably, when the flap is tucked into the recessed area 68 as shown in FIG. 3b, the distal edge 34 of the flap 24 will form a graspable tab member 90 which can be used to pull the second portion 96 of the flap 24 from the recessed area 68 and simultaneously peel the flap adhesive 56 from the unitary release member 57.

Figure 4:
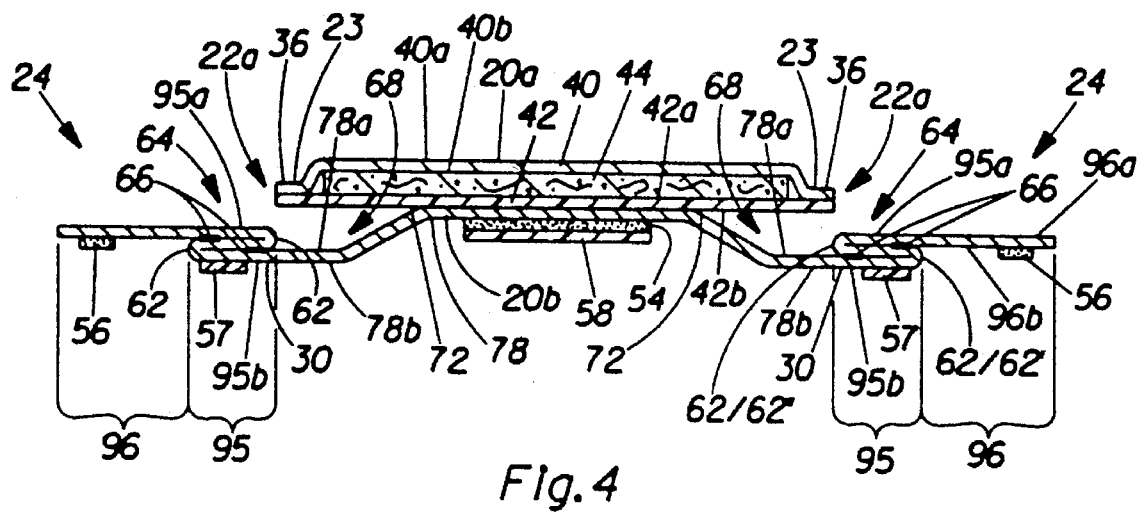
Figure 4A:
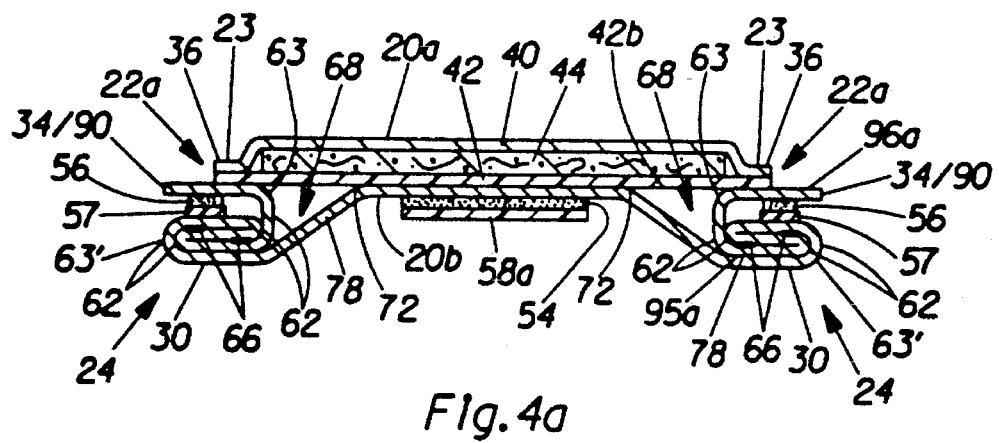
FIG. 4a is a cross-sectional view of the sanitary napkin of FIG. 4 showing the flaps tucked into the recessed areas in a folded and rolled configuration with the unitary release material superposing the flap adhesives.

A transverse, cross-sectional view of a particular preferred sanitary napkin embodiment of the present invention, is shown in FIG. 4 and 4a. The embodiment shown in FIGS. 4 and 4a is similar to the embodiment shown in FIGS. 3–3b, i.e., the flaps 24 are extensions of the retaining member 78 which is joined to the backsheet 42 of the main body portion 22 along the lines of connection 72. However, the flaps 24 are arranged in a different configuration when they are tucked, as shown in FIG. 4a, and when they are extended, as shown in FIG. 4.

Referring to FIG. 4, each flap 24 may again be thought of as having a first portion 95 and a second portion 96. The first portion 95 of the flap 24 comprises a pleat 64 which is secured by the flap pleat restraints 66, and comprises an unitary release member 57 joined to the body-facing side 95b of the first portion 95. The second portion 96 comprises a flap adhesive 56 joined to the garment-facing side 96b of the second portion 96.

The pleat 64 of the first portion 95 of the flap 24, has two longitudinally extending fold lines 62. The fold line that is closest to the proximal edge 32 of the flap 24 when the first portion 95 is unfolded, comprises a first pleat-forming fold line 62'. The fold line 62 that is located farther away from the proximal edge 32 of the flap 24 when the first portion 95 is unfolded, comprises a second pleat-forming fold line 62". The first pleat-forming fold line 62' is formed by folding the flap material toward the garment-facing side 42b of the backsheet 42. The second pleat-forming fold line 62" is also formed by folding the flap material towards the garment-facing side 42b of the backsheet 42. The pleat 64 of the first portion 95 is secured by flap pleat restraints 66 which are located substantially adjacent the mouth of each fold. The first portion 95 of the flap 24 also comprises an unitary release member 57 which is joined to the garment-facing side 95b of the first portion 95.

The first portion 95 of the flap 24 is positioned outboard of the longitudinal edge 22a of the main body portion 22 when the sanitary napkin 20 is looked at from a top plan view. This results in the first portion 95 being positioned outside of the recessed area 68 when the flap 24 is extended as shown in FIG. 4. The second portion 96 of each flap 24 comprises a flap adhesive 56. The flap adhesive 56 is positioned substantially adjacent to the distal edge 34 of the flap 24 and is positioned on the garment-facing side 96b of the second portion 96.

When the flap 24 is tucked into the recessed area 68 as shown in FIG. 4a, the second portion 96 will be folded along a first tuck-forming fold line 63 such that the flap adhesive 56 of the second portion 96 superposes the unitary release member 57 of the first portion 95. The first portion 95 and the second portion 96 are then folded toward the garment-facing side 42b of the backsheet 42 to form a second tuck-forming fold line 63'. As shown in FIG. 4a, this results in the body-facing side 95a of the first portion 95 being in substantially face to face relation with the body facing side 78' of the retaining member 78a, and the body-facing side 96a of the second portion 96 being in substantially face to face relation with the garment side 42b of the backsheet 42. Accordingly, this results in the first portion 95 and second portion 96 of the flap 24, being positioned in the recessed area 68 between the retaining member 78 and the backsheet 42 of the sanitary napkin 20. Preferably, as shown in FIG. 4a, when the flap 24 is tucked into the recessed area 68, the distal edge 34 of the flap 24 will form a graspable tap member 90.

Other methods of providing zones of differential extensibility, are discussed in greater detail in commonly-assigned, co-pending, U.S. patent application Ser. No. 07/769,891, "Absorbent Article Having Flaps and Zones of Differential Extensibility", filed Oct. 1, 1991, in the name of Bruce W. Lavash, et al., and in commonly-assigned, co-pending, U.S. patent application Ser. No. 07/832,246, "Absorbent Article Having Inwardly-Folded Pleated Flaps", filed Feb. 7, 1992, in the name of Kaoru Niihara and Thomas W. Osborn, III, which patent applications are incorporated herein by reference.

Thus, the present invention provides a sanitary napkin having flaps with a flap adhesive and a unitary release material which overlies the flap adhesive when the flap is folded along a fold line.

While particular embodiments of the present invention have been illustrated and described, it would be obvious to those skilled in the art that various other changes and modifications can be made without departing from the spirit and scope of the invention.

What is claimed is:

1. An absorbent article for wearing in a wearer's undergarment, said absorbent article having a garment side, a body-facing side, a principal longitudinal centerline that is oriented in a longitudinal direction, and a principal transverse centerline that is oriented in a transverse direction, said absorbent article comprising:

a main body portion comprising an absorbent assembly and having a length, a first longitudinal half on one side of said principal longitudinal centerline, a second longitudinal half on the other side of said principal longitudinal centerline, two spaced apart longitudinal edges, two spaced apart transverse edges, a first end region, a second end region, and a central region disposed between said first end region and said second end region, said first end region and said second end region each extending outward along said principal longitudinal centerline from said central region a distance of about ⅛ to about ⅓ the length of said main body portion, said main body portion comprising a liquid pervious topsheet, a liquid impervious backsheet joined to said topsheet, an absorbent core positioned between said topsheet and said backsheet, and a pad securement member joined to said backsheet for securing said main body portion to the wearer's undergarment; and a pair of flaps for folding under the wearer's undergarment, said flaps comprising a first flap joined to the first longitudinal half and a second flap joined to the second longitudinal half, each of said flaps being joined to said central region of said main body portion along a line of juncture outboard of said pad securement member and having a proximal edge adjacent the line of juncture, and a distal edge disposed away from the line of juncture; wherein each of said flaps has a garment side and a flap transverse centerline that passes through the central region of said main body portion and intersects the principal longitudinal centerline of the absorbent article and divides the absorbent article into four quarters, each of said quarters comprising a first portion adjacent said principal longitudinal centerline and said flap transverse centerline, and a second portion outboard of said first portion; and said second portion of at least one of said quarters of said absorbent article comprises a zone of differential extensibility, said zone of differential extensibility being capable of greater extension outward in a generally transverse direction than said first portion of said quarter, and each of said flaps comprises a flap adhesive joined to the garment side thereof and a unitary release member comprising a first surface and a second surface, said first surface being joined to the garment side of said flaps, wherein said unitary release member and said flap adhesive of each of said flaps are arranged on each of said flaps so that at least a portion of said second surface of said unitary release member superposes said flap adhesive and is removably secured thereto when each of said flaps is folded along a fold line located between said flap adhesive and said unitary release member.

2. The absorbent article of claim 1 comprising at least one retaining member comprising two end regions, a center region positioned between and joined to said end regions, and a longitudinal edge, at least a portion of each of said end regions being joined to said main body portion at a point of connection, at least a portion of said center region being decoupled from said main body portion to form a first recessed area and a second recessed area between said center region of said retaining member and said main body portion, said first recessed area being located on said first longitudinal half of said main body portion, said second recessed area being located on said second longitudinal half of said main body portion, and at least a portion of said first flap can be tucked into said first recessed area.

3. The absorbent article of claim 2 wherein said main body portion comprises two retaining members joined to said absorbent assembly to form two recessed areas.

4. The absorbent article of claims 2 wherein said retaining member comprises a discrete piece of material joined to said main body portion.

5. The absorbent article of claim 2 wherein said retaining member comprises at least a portion of said backsheet.

6. An absorbent article for wearing in a wearer's undergarment, said absorbent article having a principal longitudinal centerline that is oriented in a longitudinal direction and divides said article into a first longitudinal half and a second longitudinal half, a principal transverse centerline that is oriented in a transverse direction, a body-facing side and a garment side, said absorbent article comprising:

a main body portion comprising a liquid pervious topsheet, a liquid impervious backsheet joined to said topsheet, and an absorbent core positioned between said topsheet and said backsheet, and a pad securement member joined to a portion of said backsheet, and having two spaced apart longitudinal edges, a first end region, a second end region, and a central region disposed between said first end region and said second end region, said first end region and said second end region each extending outward along said principal longitudinal centerline form said central region a distance of about ⅛ to about ⅓ the length of said main body portion, and at least one retaining member joined at a line of connection to said backsheet to form a first recessed area located on said first longitudinal half of said article and a second recessed area located on said second longitudinal half of said article, each of said first recessed area and said second recessed area being formed between said retaining member and said backsheet and having a mouth;

a pair of flaps for folding under the wearer's undergarment, a first flap joined to the first longitudinal half and a second flap joined to the second longitudinal half, each of said flaps being joined to said central region of said main body portion along a line of juncture and having a transverse centerline, a proximal edge adjacent said line of juncture, a distal edge disposed away from said line of juncture, a flap adhesive joined to the garment side thereof, and a unitary release member having a first surface and a second surface, said first surface being joined to the garment side thereof so that at least a portion of said second surface of said unitary release member superposes said flap adhesive and is removably secured thereto when said flap is folded along a fold line located between said flap adhesive and said unitary release material.

7. A method of using an absorbent article comprising the steps of:

providing the absorbent article of claim 6, tucking at least a portion of said first flap into said first recessed area and at least a portion of said second flap into said second recessed area;

providing an undergarment comprising a front section; a back section; and a crotch portion which joins said front section and said back section, said crotch portion comprising two side edges, a center crotch portion, an inside, and an underside;

positioning said absorbent article in said inside of said crotch portion of said undergarment such that said main body portion is positioned in said center crotch portion with one end of said main body portion extending towards said front section and the other end of said main body portion extending towards said back section, and said pad securement member is secured to said inside of said crotch portion of said undergarment.

8. The absorbent article of claim 6 wherein at least a portion of said first flap is tucked into said mouth of said first recessed area and at least a portion of said second flap is tucked into said mouth of said second recessed area.

9. The absorbent article of claim 8 wherein said flaps are joined to at least a portion of said backsheet.

10. The absorbent article of claim 8 wherein said flaps are joined to at least a portion of said retaining member.

11. The absorbent article of claim 8 wherein each said flap comprises a graspable tab portion.

12. The absorbent article of claim 11 wherein said graspable tab portion extends laterally outward from said longitudinal edge of said main body portion at least two to three millimeters.

13. The absorbent article of claim 11 wherein said graspable tab portion extends laterally outward from said longitudinal edge of said main body portion at least five to ten millimeters.

14. The absorbent article of claim 11 wherein said graspable tab portion comprises said distal edge of said flaps.

15. The absorbent article for wearing in a wearer's undergarment, said absorbent article having a garment side, a body-facing side, said absorbent article comprising:

a main body portion comprising an absorbent assembly and having a length, a principal longitudinal centerline that is oriented in a longitudinal direction and divides said main body portion into a first longitudinal half and a second longitudinal half, a principal transverse centerline that is oriented in a transverse direction, two spaced apart longitudinal edges, two spaced apart transverse edges, a first end region, a second end region, and a central region disposed between said first end region and said second end region, said first end region and said second end region each extending outward along said principal longitudinal centerline from said central region a distance of about ⅛ to about ⅓ the length of said main body portion;

a pair of flaps for folding under the wearer's undergarment, said pair of flaps comprising a first flap joined to said central region of the first longitudinal half of said main body portion at a line of juncture and said second flap joined to said central region of the second longitudinal half of said main body portion at a line of juncture, said first and second flaps each having a garment side, and each comprising a proximal edge substantially adjacent the line of juncture, a distal edge disposed away from the line of juncture, and a flap adhesive joined to the garment side of said flaps for securing said flaps to the wearer's undergarment; and a first unitary release member comprising a first surface and a second surface, said first surface being joined to the garment side of said first flap, at least a portion of said second surface of said first unitary release member superposing and being removably secured to said flap adhesive of said first flap and a second unitary release member comprising a first surface and a second surface, said first surface being joined to the garment side of said second flap, at least a portion of said second surface of said second unitary release member superposing and being removably secured to said flap adhesive of said second flap, wherein said first unitary release member comprises a first portion and a second portion hingedly joined to said first portion, at least a part of said first surface of said first portion of said first unitary release member being joined to said garment side of said first flap at a bond site, and at least a part of said first surface of said second portion of said first unitary release member superposing and being removably secured to said flap adhesive; and said second unitary release member comprises a first portion and a second portion hingedly joined to said first portion, at least a part of said first surface of said first portion of said second unitary release member being joined to said garment side of said second flap at a bond site, and at least a part of said first surface of said second portion of said second unitary release member superposing and being removably secured to said flap adhesive.

16. The absorbent article of claim 15 additionally comprising:

a first bonding material joined thereto which can be secured to said second surface of said second portion of said first unitary release member so that said second portion of said first unitary release member may be secured away from said flap adhesive of said first flap when said first surface of said second portion of said first unitary release member has been removed from said flap adhesive of said first flap; and a second bonding material joined thereto which can be secured to said second surface of said second portion of said second unitary release member so that said second portion of said second unitary release member may be secured away from said flap adhesive of said second flap when said first surface of said second portion of said second unitary release member has been removed from said flap adhesive of said second flap.

17. A method of using an absorbent article comprising the steps of:

providing an absorbent article having a body-facing side and a garment side, said absorbent article comprising: a main body portion comprising a liquid pervious topsheet, a liquid impervious backsheet joined to said topsheet, and an absorbent core positioned between said topsheet and said backsheet, two spaced apart longitudinal edges, and at least one retaining member joined at a line of connection to said backsheet to form two recessed areas between said retaining member and said backsheet, each of said recessed areas having a mouth; a pair of flaps, each flap being joined to said main body portion at a line of juncture and extending laterally outward from a longitudinal edge of said main body portion, said flaps having a transverse centerline, said flaps comprising a proximal edge adjacent said longitudinal edge of said main body portion, a distal edge disposed away from said longitudinal edge of said main body portion, at least one fold line, a flap securement member comprising a flap adhesive, and an integral release member joined to said flap such that said integral release member superposes said flap adhesive and is removably secured thereto when said flap is folded along said fold line; and at least a portion of one of said flaps being tucked into said mouth of one of said recessed areas, and at least a portion of the other of said flaps being tucked into said mouth of the other of said recessed areas;

providing an undergarment comprising a front section; a back section; and a crotch portion which joins said front section and said back section, said crotch portion comprising two side edges, a center crotch portion, an inside, and an underside;

positioning said absorbent article in said inside of said crotch portion of said undergarment such that said main body portion is positioned in said center crotch portion with one end of said main body portion extending towards said front section and the other end of said main body portion extending towards said back section, and said pad securement member is secured to said inside of said crotch portion of said undergarment;

removing each of said flaps from said recessed areas such that said unitary release member peels from said flap securement member exposing said flap adhesive;

wrapping said flaps around said side edges of said undergarment; and securing said flap adhesive of each of said flaps to said underside of said crotch portion of said undergarment.

* * * * *